US011441188B2

(12) United States Patent
Sanders et al.

(10) Patent No.: US 11,441,188 B2
(45) Date of Patent: *Sep. 13, 2022

(54) METHODS FOR DETECTING DNA MUTATIONS USING MITRA TIP EXTRACTION

(71) Applicant: Quest Diagnostics Investments LLC, Secaucus, NJ (US)

(72) Inventors: Heather Sanders, San Juan Capistrano, CA (US); Nigel J. Clarke, Vista, CA (US)

(73) Assignee: Quest Diagnostics Investments LLC, Secaucus, NJ (US)

( * ) Notice: Subject to any disclaimer, the term of this patent is extended or adjusted under 35 U.S.C. 154(b) by 861 days.

This patent is subject to a terminal disclaimer.

(21) Appl. No.: 15/811,515

(22) Filed: Nov. 13, 2017

(65) Prior Publication Data

US 2018/0135135 A1    May 17, 2018

Related U.S. Application Data

(60) Provisional application No. 62/422,334, filed on Nov. 15, 2016.

(51) Int. Cl.
*C12Q 1/6886* (2018.01)
*C12Q 1/6806* (2018.01)
(Continued)

(52) U.S. Cl.
CPC ....... *C12Q 1/6886* (2013.01); *C12N 15/1058* (2013.01); *C12N 15/1065* (2013.01);
(Continued)

(58) Field of Classification Search
CPC ............ C12N 15/1058; C12N 15/1065; C12Q 1/6806; C12Q 1/6886; C12Q 2527/125;
(Continued)

(56) References Cited

U.S. PATENT DOCUMENTS

2011/0203688 A1    8/2011 Reed et al.
2012/0192298 A1    7/2012 Weinstein et al.
(Continued)

FOREIGN PATENT DOCUMENTS

JP    2008-546404 A    12/2008
JP    2013-528058 A    7/2013
(Continued)

OTHER PUBLICATIONS

Qiagen® (Genomic DNA Handbook, Jun. 2015) (Year: 2015).*
(Continued)

*Primary Examiner* — Jeremy C Flinders
(74) *Attorney, Agent, or Firm* — Foley & Lardner LLP

(57) ABSTRACT

The present disclosure provides rapid and non-invasive methods for determining whether a patient exhibiting cancer symptoms, or at risk for hereditary cancers such as breast cancer, ovarian cancer, colon cancer, or skin cancer, will benefit from treatment with one or more therapeutic agents. These methods are based on detecting hereditary cancer-related mutations in small-volume dried biological fluid samples that are collected using a volumetric absorptive microsampling device (e.g., MITRA Tip). Kits for use in practicing the methods are also provided.

18 Claims, 9 Drawing Sheets

(51) Int. Cl.
| | |
|---|---|
| *C12N 15/10* | (2006.01) |
| *G01N 33/487* | (2006.01) |
| *G01N 33/49* | (2006.01) |
| *G01N 33/53* | (2006.01) |
| *G01N 33/533* | (2006.01) |
| *A61P 43/00* | (2006.01) |

(52) U.S. Cl.
CPC ....... *C12Q 1/6806* (2013.01); *G01N 33/4875* (2013.01); *G01N 33/49* (2013.01); *G01N 33/533* (2013.01); *G01N 33/5308* (2013.01); *C12Q 2527/125* (2013.01); *C12Q 2600/112* (2013.01); *C12Q 2600/118* (2013.01); *C12Q 2600/156* (2013.01); *C12Q 2600/16* (2013.01)

(58) Field of Classification Search
CPC ........ C12Q 2600/112; C12Q 2600/118; C12Q 2600/156; C12Q 2600/16; G01N 33/4875; G01N 33/49; G01N 33/5308; G01N 33/533
See application file for complete search history.

(56) References Cited

U.S. PATENT DOCUMENTS

| | | | |
|---|---|---|---|
| 2013/0116597 A1* | 5/2013 | Rudge | A61B 5/150305 600/575 |
| 2013/0237432 A1 | 9/2013 | Li et al. | |
| 2016/0281166 A1 | 9/2016 | Bhattacharjee et al. | |
| 2018/0089373 A1* | 3/2018 | Matsuguchi | G16B 99/00 |

FOREIGN PATENT DOCUMENTS

| | | |
|---|---|---|
| JP | 2013-529472 A | 7/2013 |
| WO | WO-2006/137733 A1 | 12/2006 |
| WO | WO-2011/155833 A2 | 12/2011 |
| WO | WO-2013/067520 A1 | 5/2013 |
| WO | WO-2016/037142 A1 | 3/2016 |
| WO | WO-2016/134324 A1 | 8/2016 |
| WO | WO-2017/060271 A1 | 4/2017 |
| WO | WO-2017/161201 A1 | 9/2017 |

OTHER PUBLICATIONS

Eiermann et al. (Annals of Oncology 12 (Suppl. I): S57-S62, 2001) (Year: 2001).*

Wong et al. (Current Protocols in Molecular Biology 7.11.1-7.11.11) (Year: 2013).*

Houbart et al.: "Volumetric Absorptive Microsampling for Hepcidin Peptide Extraction from Whole Blood"; LCGC North America, May 1, 2016, vol. 34, Iss. 5, pp. 340-347, entire document.

International Search Report dated Feb. 16, 2018 as issued in corresponding International Application No. PCT/US2017/061316.

Denniff et al., "Volumetric Absorptive Microsampling: A Dried Sample Collection Technique for Quantitative Bioanalysis," Analytical Chemistry, Aug. 19, 2014, 86(16):8489-8495.

John et al., "Procedures for Analysis of Dried Plasma Using Microsampling Devices to Detect Sulfur Mustard-Albumin Adducts for Verification of Poisoning," Analytical Chemistry, Aug. 15, 2016, 88(17):8787-8794.

Luo et al., "Evaluation of two blood microsampling approaches fordrug discovery PK studies in rats," Bioanalysis, Sep. 1, 2015, 7(18):2345-2359.

Nicholls et al., "Evaluation of the Mitra™ microsampling device against Dried Blood Spot cards for measurement of 25(OH)D$_3$ by LC/MS-MS," Conference Proceedings Article, Jan. 1, 2016, 2 pages.

Spooner et al., "A device for dried blood microsampling in quantitative bioanalysis: overcoming the issues associated with blood hematocrit," Bioanalysis, Apr. 1, 2015, 7(6):653-659.

Supplementary European Search Report dated Jul. 24, 2020 in EP 17871115.6.

Denniff et al., "Volumetric Absorptive Microsampling: A Dried Sample Collection Technique for Quantitative Bioanalysis," Analytical Chemistry, Jul. 24, 2014, 86:8489-8495.

MyVantage(TM) Hereditary Comprehensive Cancer Panel, Oct. 21, 2016, retrieved Jan. 21, 2022 from https://www.ncbi.nlm.nih.gov/gtr/tests/552183.1/methodology, 5 pages.

Office Action and Search Report dated Jan. 17, 2022 in CN 201780083031.X, with English translation.

Office Action dated Feb. 1, 2022 in JP 2019-546777, with English translation.

Anslinger et al., "Application of the BioRobot EZ1 in a forensic laboratory," Legal medicine, 2005, 7:164-168.

Office Action dated Sep. 21, 2021 in JP 2019-546777, with English translation.

How much DNA and RNA can be expected from human blood cells? [online], Qiagen, [retrieved on May 18, 2022], Retrieved from the Internet, URL <https://www.qiagen.com/jp/resources/faq?id=01070e31-3a4c-42d7-870c-e8005285889f&lang=en>.

Office Action dated May 31, 2022 in JP 2019-546777, with English translation.

* cited by examiner

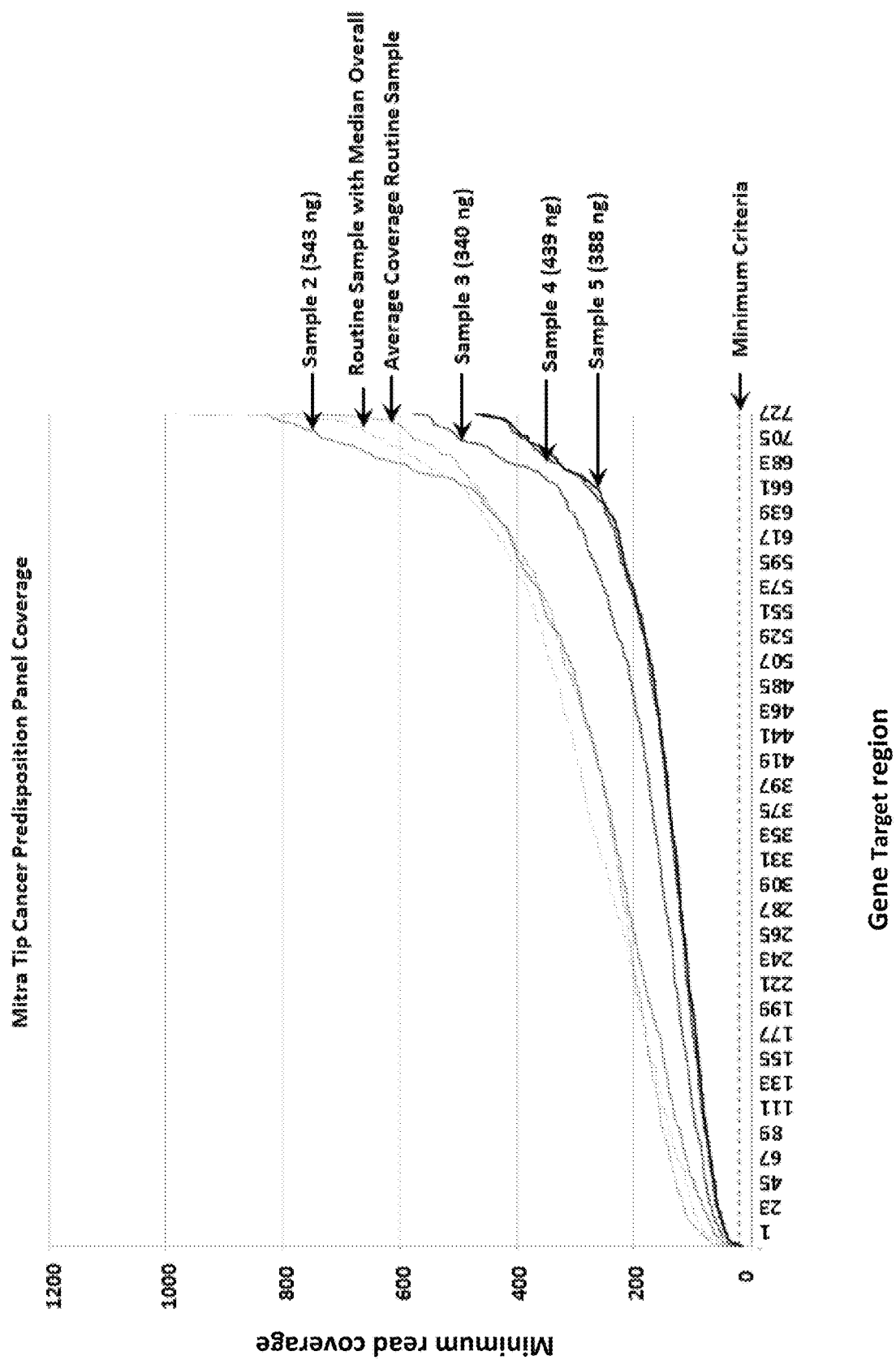

METHODS FOR DETECTING DNA MUTATIONS USING MITRA TIP EXTRACTION

TECHNICAL FIELD

The present disclosure provides methods for determining whether a patient exhibiting cancer symptoms, or at risk for hereditary cancers such as breast cancer, ovarian cancer, colon cancer, or skin cancer, will benefit from treatment with one or more therapeutic agents. These methods are based on detecting hereditary cancer-related mutations in small-volume dried biological fluid samples that are collected using a volumetric absorptive microsampling device. Alterations in target nucleic acid sequences corresponding to one or more genes associated with hereditary cancers may be detected using next generation sequencing (NGS). Kits for use in practicing the methods are also provided.

BACKGROUND

The following description of the background of the present disclosure is provided simply to aid the reader in understanding the disclosure and is not admitted to describe or constitute prior art to the present disclosure.

Hereditary cancers account for 5-10% of all cancers, and arise due to highly penetrant germline mutations. The most common hereditary cancers are breast cancer, ovarian cancer, colon cancer, and skin cancer. Inheriting a genetic mutation or pathogenic variant increases a patient's risk for developing cancer. Accordingly, determining whether a cancer arises due to an inherited pathogenic variant may be useful in assessing a patient's risk for developing cancer and may help uncover options for cancer screening, prevention, and therapy.

Next generation sequencing (NGS) is extensively used in cancer diagnostics because of its ability to detect multiple gene alterations in a single assay in a high throughput fashion. However, the procedures associated with collecting and preparing nucleic acids from biological samples (e.g., blood) are usually cumbersome, and often require specialized equipment or technical skill. Further, critically ill patients, such as cancer patients, are unable to provide large volumes of blood for recurrent testing.

Thus, there is a need for rapid and non-invasive methods for determining whether a patient is at risk for hereditary cancers such as breast cancer, ovarian cancer, colon cancer, or skin cancer.

SUMMARY

In one aspect, the present disclosure provides a method for detecting at least one mutation in a plurality of hereditary cancer-related genes in a dried biological fluid sample comprising (a) extracting genomic DNA from a dried biological fluid sample eluted from an absorbent tip of a microsampling device; (b) generating a library comprising amplicons corresponding to each of the plurality of hereditary cancer-related genes, said plurality of hereditary cancer-related genes comprising APC, ATM, BARD1, BMPR1A, BRCA1, BRCA2, BRIP1, CDH1, CDK4, CDKN2A (p14ARF and p16), CHEK2, EPCAM MEN1, MLH1, MSH2, MSH6, MUTYH, NBN, NF1, PALB2, PMS2, POLD1, POLE, PTEN, RAD51C, RAD51D, RET, SDHB, SDHC, SDHD, SMAD4, STK11, TP53, and VHL, wherein an adapter sequence is ligated to the ends of the plurality of amplicons; and (c) detecting at least one mutation in at least one of the plurality of amplicons using high throughput massive parallel sequencing. In some embodiments, the dried biological fluid sample is dried plasma, dried serum, or dried whole blood. In some embodiments, the dried biological fluid sample comprises an anticoagulant (e.g., EDTA, heparin). In certain embodiments, the dried biological fluid sample is obtained from a patient having, or is suspected of having a hereditary cancer. The hereditary cancer may be breast cancer, ovarian cancer, colon cancer, or skin cancer.

Additionally or alternatively, in some embodiments, the dried biological fluid sample on the absorbent tip of the microsampling device is collected from a patient via fingerstick. In certain embodiments, the microsampling device is a MITRA® tip. Elution of the dried biological fluid sample may be performed by contacting the absorbent tip of the microsampling device with a lysis buffer and Proteinase K. In certain embodiments, the lysis buffer comprises guanidine hydrochloride, Tris.Cl, EDTA, Tween 20, and Triton X-100. In a further embodiment, the lysis buffer comprises 800 mM guanidine hydrochloride; 30 mM Tris.Cl, pH 8.0; 30 mM EDTA, pH 8.0; 5% Tween 20; and 0.5% Triton X-100. In other embodiments, the lysis buffer comprises 2.5-10% sodium dodecyl sulphate.

Additionally or alternatively, in some embodiments, elution of the dried biological fluid sample is performed by contacting the absorbent tip of the microsampling device with the lysis buffer for up to 15 minutes at 90° C. Additionally or alternatively, in certain embodiments, elution of the dried biological fluid sample is performed by contacting the absorbent tip of the microsampling device with Proteinase K for up to 1 hour at 56° C. In other embodiments, elution of the dried biological fluid sample is performed by contacting the absorbent tip of the microsampling device with Proteinase K for up to 16-18 hours at 56° C. In some embodiments, the sample volume of the microsampling device is no more than 10-20 µL.

In some embodiments of the method, no more than 400 ng of genomic DNA is eluted from the absorbent tip of the microsampling device. In other embodiments of the method, about 100 ng to about 400 ng of genomic DNA is eluted from the absorbent tip of the microsampling device.

In certain embodiments, the high throughput massive parallel sequencing is performed using pyrosequencing, reversible dye-terminator sequencing, SOLiD sequencing, Ion semiconductor sequencing, Helioscope single molecule sequencing, sequencing by synthesis, sequencing by ligation, or SMRT™ sequencing. In some embodiments of the method, the adapter sequence is a P5 adapter, P7 adapter, P1 adapter, A adapter, or Ion Xpress™ barcode adapter.

Additionally or alternatively, in some embodiments, the plurality of amplicons further comprises a unique index sequence. In certain embodiments, the plurality of amplicons are enriched using a bait set comprising nucleic acid sequences that are complementary to at least one of the plurality of amplicons. In some embodiments, the nucleic acid sequences of the bait set are RNA baits, DNA baits, or a combination thereof.

In another aspect, the present disclosure provides a method for detecting at least one mutation in a plurality of hereditary cancer-related genes in a dried biological fluid sample comprising isolating genomic DNA from a dried biological fluid sample eluted from an absorbent tip of a microsampling device with a lysis buffer and Proteinase K, wherein the plurality of hereditary cancer-related genes comprises APC, ATM, BARD1, BMPR1A, BRCA1, BRCA2, BRIP1, CDH1, CDK4, CDKN2A (p14ARF and p16), CHEK2, EPCAM, MEN1, MLH1, MSH2, MSH6, MUTYH, NBN, NF1, PALB2, PMS2, POLD1, POLE, PTEN, RAD51C, RAD51D, RET, SDHB, SDHC, SDHD, SMAD4, STK11, TP53, and VHL. In certain embodiments, the at least one mutation in the plurality of hereditary cancer-related genes is detected using high throughput massive parallel sequencing. In some embodiments, the lysis buffer comprises guanidine hydrochloride, Tris.Cl, EDTA, Tween 20, and Triton X-100.

In one aspect, the present disclosure provides a method for selecting a patient exhibiting cancer symptoms, or a patient at risk for hereditary cancer, for treatment with an anti-cancer therapeutic agent comprising (a) eluting a dried blood sample under conditions that result in the release of genomic DNA from blood cells, wherein the dried blood sample is collected from the patient with a volumetric absorptive microsampling device; (b) isolating genomic DNA from the eluted dried blood sample; (c) generating a library comprising amplicons corresponding to each of a plurality of hereditary cancer-related genes comprising APC, ATM, BARD1, BMPR1A, BRCA1, BRCA2, BRIP1, CDH1, CDK4, CDKN2A (p14ARF and p16), CHEK2, EPCAM, MEN1, MLH1, MSH2, MSH6, MUTYH, NBN, NF1, PALB2, PMS2, POLD1, POLE, PTEN, RAD51C, RAD51D, RET, SDHB, SDHC, SDHD, SMAD4, STK11, TP53, and VHL, wherein an adapter sequence is ligated to the ends of the plurality of amplicons; (d) detecting at least one mutation in at least one of the plurality of amplicons using high throughput massive parallel sequencing; and (e) selecting the patient for treatment with an anti-cancer therapeutic agent, if a mutation in at least one of the plurality of amplicons corresponding to one or more of APC, ATM, BARD1, BMPR1A, BRCA1, BRCA2, BRIP1, CDH1, CDK4, CDKN2A (p14ARF and p16), CHEK2, EPCAM MEN1, MLH1, MSH2, MSH6, MUTYH, NBN, NF1, PALB2, PMS2, POLD1, POLE, PTEN, RAD51C, RAD51D, RET, SDHB, SDHC, SDHD, SMAD4, STK11, TP53, and VHL is detected. In some embodiments, the volumetric absorptive microsampling device is a MITRA® tip. In certain embodiments, the patient has, or is at risk for a hereditary cancer selected from the group consisting of breast cancer, ovarian cancer, skin cancer, or colon cancer.

In any of the above embodiments, the anti-cancer therapeutic agent is one or more agents selected from the group consisting of cyclophosphamide, fluorouracil (or 5-fluorouracil or 5-FU), methotrexate, edatrexate (10-ethyl-10-deazaaminopterin), thiotepa, carboplatin, cisplatin, taxanes, paclitaxel, protein-bound paclitaxel, docetaxel, vinorelbine, tamoxifen, raloxifene, toremifene, fulvestrant, gemcitabine, irinotecan, ixabepilone, temozolmide, topotecan, vincristine, vinblastine, eribulin, mutamycin, capecitabine, anastrozole, exemestane, letrozole, leuprolide, abarelix, buserlin, goserelin, megestrol acetate, risedronate, pamidronate, ibandronate, alendronate, denosumab, zoledronate, trastuzumab, tykerb, anthracyclines, bevacizumab, aldesleukin, cobimetinib, dabrafenib, dacarbazine, talimogene laherparepvec, imiquimod, recombinant Interferon Alfa-2b, ipilimumab, pembrolizumab, trametinib, nivolumab, peginterferon Alfa-2b, sonidegib, vismodegib, vemurafenib, cetuximab, irinotecan hydrochloride, leucovorin calcium, trifluridine and tipiracil hydrochloride, oxaliplatin, panitumumab, ramucirumab, regorafenib, and ziv-aflibercept.

Also disclosed herein are kits for detecting at least one mutation in a plurality of hereditary cancer-related genes in a dried biological fluid sample comprising a skin puncture tool, a volumetric absorptive microsampling device, a lysis buffer, and proteinase K, wherein the plurality of hereditary cancer-related genes comprises APC, ATM, BARD1, BMPR1A, BRCA1, BRCA2, BRIP1, CDH1, CDK4, CDKN2A (p14ARF and p16), CHEK2, EPCAM, MEN1, MLH1, MSH2, MSH6, MUTYH, NBN, NF1, PALB2, PMS2, POLD1, POLE, PTEN, RAD51C, RAD51D, RET, SDHB, SDHC, SDHD, SMAD4, STK11, TP53, and VHL. The lysis buffer may comprise guanidine hydrochloride, Tris.Cl, EDTA, Tween 20, and Triton X-100.

In some embodiments, the kits of the present technology further comprise one or more primer pairs that hybridize to one or more regions or exons of one or more of the plurality of hereditary cancer-related genes. Additionally or alternatively, in some embodiments, the kits of the present technology further comprise one or more bait sequences that hybridize to one or more regions or exons of one or more of the plurality of hereditary cancer-related genes.

In any of the above embodiments of the kits of the present technology, the volumetric absorptive microsampling device is a MITRA® tip.

BRIEF DESCRIPTION OF THE DRAWINGS

FIG. 2(a) shows the minimum read coverage per target region obtained from dried blood samples eluted from MITRA® tips on a 34-gene cancer predisposition panel (MyVantage™ Hereditary Comprehensive Cancer Panel).

DETAILED DESCRIPTION

Figure 1:
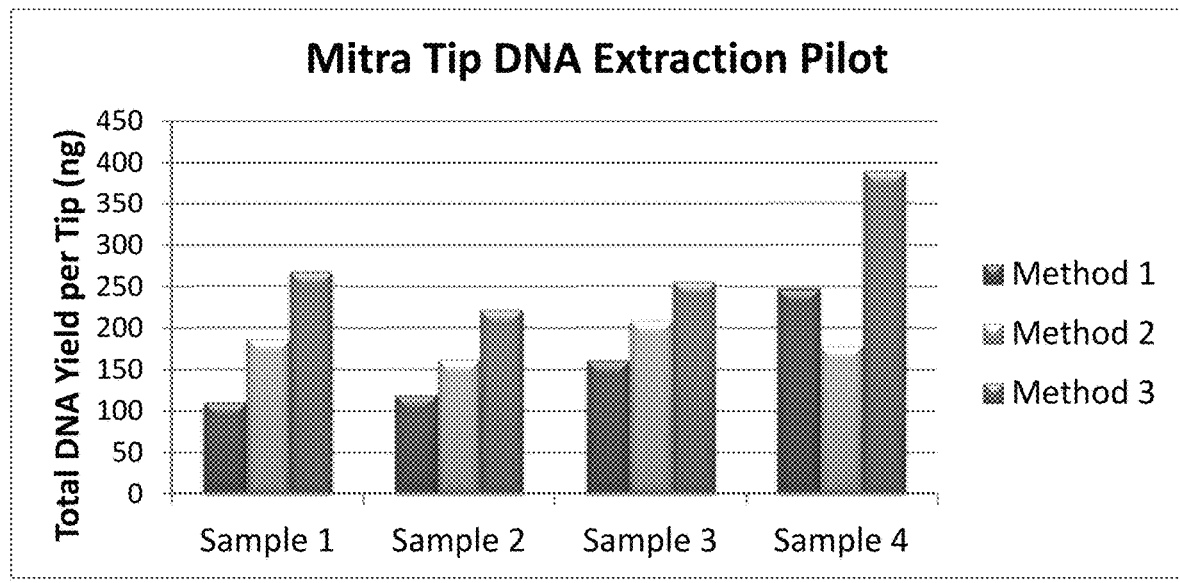
FIG. 1 shows DNA yield per MITRA® tip using the three different extraction methods as described in Example 1.

The present disclosure provides methods for determining whether a patient exhibiting cancer symptoms, or at risk for hereditary cancers such as breast cancer, ovarian cancer, colon cancer, or skin cancer, will benefit from treatment with one or more therapeutic agents. These methods are based on detecting hereditary cancer-related mutations in small-volume dried biological fluid samples that are collected using a volumetric absorptive microsampling device. Further, the methods disclosed herein retain their analytical sensitivity when used on dried biological fluid samples containing anticoagulants, such as EDTA, which are known PCR-inhibitors. See Huggett et al., *BMC Res Notes*. 1: 70 (2008). Kits for use in practicing the methods are also provided.

Definitions

Unless otherwise defined, all technical and scientific terms used herein have the same meaning as commonly understood by one of ordinary skill in the art to which the present technology belongs.

As used herein, the term "about" in reference to a number is generally taken to include numbers that fall within a range of 1%-10% in either direction (greater than or less than) of the number unless otherwise stated or otherwise evident from the context.

The term "adapter" refers to a short, chemically synthesized, nucleic acid sequence which can be used to ligate to the end of a nucleic acid sequence in order to facilitate attachment to another molecule. The adapter can be single-stranded or double-stranded. An adapter can incorporate a short (typically less than 50 base pairs) sequence useful for PCR amplification or sequencing.

As used herein, the "administration" of a therapeutic agent or drug to a subject includes any route of introducing or delivering to a subject a compound to perform its intended function. Administration can be carried out by any suitable route, including orally, intranasally, parenterally (intravenously, intramuscularly, intraperitoneally, or subcutaneously), or topically. Administration includes self-administration and the administration by another.

As used herein, an "alteration" of a gene or gene product (e.g., a marker gene or gene product) refers to the presence of a mutation or mutations within the gene or gene product, e.g., a mutation, which affects the quantity or activity of the gene or gene product, as compared to the normal or wild-type gene. The genetic alteration can result in changes in the quantity, structure, and/or activity of the gene or gene product in a cancer tissue or cancer cell, as compared to its quantity, structure, and/or activity, in a normal or healthy tissue or cell (e.g., a control). For example, an alteration which is associated with cancer can have an altered nucleotide sequence (e.g., a mutation), amino acid sequence, chromosomal translocation, intra-chromosomal inversion, copy number, expression level, protein level, protein activity, in a cancer tissue or cancer cell, as compared to a normal, healthy tissue or cell. Exemplary mutations include, but are not limited to, point mutations (e.g., silent, missense, or nonsense), deletions, insertions, inversions, linking mutations, duplications, translocations, inter- and intra-chromosomal rearrangements. Mutations can be present in the coding or non-coding region of the gene. In certain embodiments, the alterations are associated with a phenotype, e.g., a cancerous phenotype (e.g., one or more of cancer risk, cancer progression, cancer treatment or resistance to cancer treatment).

As used herein, the terms "amplify" or "amplification" with respect to nucleic acid sequences, refer to methods that increase the representation of a population of nucleic acid sequences in a sample. Copies of a particular target nucleic acid sequence generated in vitro in an amplification reaction are called "amplicons" or "amplification products". Amplification may be exponential or linear. A target nucleic acid may be DNA (such as, for example, genomic DNA and cDNA) or RNA. While the exemplary methods described hereinafter relate to amplification using polymerase chain reaction (PCR), numerous other methods such as isothermal methods, rolling circle methods, etc., are well known to the skilled artisan. The skilled artisan will understand that these other methods may be used either in place of, or together with, PCR methods. See, e.g., Saiki, "*Amplification of Genomic DNA*" in PCR PROTOCOLS, Innis et al., Eds., Academic Press, San Diego, Calif. 1990, pp 13-20; Wharam, et al., *Nucleic Acids Res.* 29(11):E54-E54 (2001).

"Bait", as used herein, is a type of hybrid capture reagent that retrieves target nucleic acid sequences for sequencing. A bait can be a nucleic acid molecule, e.g., a DNA or RNA molecule, which can hybridize to (e.g., be complementary to), and thereby allow capture of a target nucleic acid. In one embodiment, a bait is an RNA molecule (e.g., a naturally-occurring or modified RNA molecule); a DNA molecule (e.g., a naturally-occurring or modified DNA molecule), or a combination thereof. In other embodiments, a bait includes a binding entity, e.g., an affinity tag, that allows capture and separation, e.g., by binding to a binding entity, of a hybrid formed by a bait and a nucleic acid hybridized to the bait. In one embodiment, a bait is suitable for solution phase hybridization.

As used herein, "bait set" refers to one or a plurality of bait molecules.

The terms "cancer" or "tumor" are used interchangeably and refer to the presence of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells can exist alone within an animal, or can be a non-tumorigenic cancer cell. As used herein, the term "cancer" includes premalignant, as well as malignant cancers.

The terms "complement", "complementary" or "complementarity" as used herein with reference to polynucleotides (i.e., a sequence of nucleotides such as an oligonucleotide or a target nucleic acid) refer to the Watson/Crick base-pairing rules. The complement of a nucleic acid sequence as used herein refers to an oligonucleotide which, when aligned with the nucleic acid sequence such that the 5' end of one sequence is paired with the 3' end of the other, is in "antiparallel association." For example, the sequence "5'-A-G-T-3'" is complementary to the sequence "3'-T-C-A-5'." Certain bases not commonly found in naturally-occurring nucleic acids may be included in the nucleic acids described herein. These include, for example, inosine, 7-deazaguanine, Locked Nucleic Acids (LNA), and Peptide Nucleic Acids (PNA). Complementarity need not be perfect; stable duplexes may contain mismatched base pairs, degenerative, or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs. A complement sequence can also be an RNA sequence complementary to the DNA sequence or its complement sequence, and can also be a cDNA.

The term "substantially complementary" as used herein means that two sequences hybridize under stringent hybridization conditions. The skilled artisan will understand that substantially complementary sequences need not hybridize along their entire length. In particular, substantially complementary sequences may comprise a contiguous sequence of bases that do not hybridize to a target sequence, positioned 3' or 5' to a contiguous sequence of bases that hybridize under stringent hybridization conditions to a target sequence.

As used herein, a "control" is an alternative sample used in an experiment for comparison purpose. A control can be "positive" or "negative." A "control nucleic acid sample" or "reference nucleic acid sample" as used herein, refers to nucleic acid molecules from a control or reference sample. In certain embodiments, the reference or control nucleic acid sample is a wild type or a non-mutated DNA or RNA sequence. In certain embodiments, the reference nucleic acid sample is purified or isolated (e.g., it is removed from its natural state). In other embodiments, the reference nucleic acid sample is from a non-tumor sample, e.g., a blood control, a normal adjacent tumor (NAT), or any other non-cancerous sample from the same or a different subject.

As used herein, the term "detecting" refers to determining the presence of a mutation or alteration in a nucleic acid of interest in a sample. Detection does not require the method to provide 100% sensitivity.

As used herein, the term "effective amount" refers to a quantity sufficient to achieve a desired therapeutic and/or prophylactic effect, e.g., an amount which results in the prevention of, or a decrease in hereditary cancer, or one or more symptoms associated with hereditary cancer. In the context of therapeutic or prophylactic applications, the amount of a therapeutic agent administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. As used herein, a "therapeutically effective amount" of a therapeutic drug or agent is meant levels in which the physiological effects of a hereditary cancer such as breast cancer, ovarian cancer, colon cancer, or skin cancer are, at a minimum, ameliorated. A therapeutically effective amount can be given in one or more administrations.

As used herein, the terms "extraction" or "isolation" refer to any action taken to separate nucleic acids from other cellular material present in the sample. The term extraction or isolation includes mechanical or chemical lysis, addition of detergent or protease, or precipitation and removal of other cellular material.

"Gene" as used herein refers to a DNA sequence that comprises regulatory and coding sequences necessary for the production of an RNA, which may have a non-coding function (e.g., a ribosomal or transfer RNA) or which may include a polypeptide or a polypeptide precursor. The RNA or polypeptide may be encoded by a full length coding sequence or by any portion of the coding sequence so long as the desired activity or function is retained. Although a sequence of the nucleic acids may be shown in the form of DNA, a person of ordinary skill in the art recognizes that the corresponding RNA sequence will have a similar sequence with the thymine being replaced by uracil, i.e., "T" is replaced with "U."

The term "hybridize" as used herein refers to a process where two substantially complementary nucleic acid strands (at least about 65% complementary over a stretch of at least 14 to 25 nucleotides, at least about 75%, or at least about 90% complementary) anneal to each other under appropriately stringent conditions to form a duplex or heteroduplex through formation of hydrogen bonds between complementary base pairs. Hybridizations are typically and preferably conducted with probe-length nucleic acid molecules, preferably 15-100 nucleotides in length, more preferably 18-50 nucleotides in length. Nucleic acid hybridization techniques are well known in the art. See, e.g., Sambrook, et al., 1989, *Molecular Cloning: A Laboratory Manual*, Second Edition, Cold Spring Harbor Press, Plainview, N.Y. Hybridization and the strength of hybridization (i.e., the strength of the association between the nucleic acids) is influenced by such factors as the degree of complementarity between the nucleic acids, stringency of the conditions involved, and the thermal melting point ($T_m$) of the formed hybrid. Those skilled in the art understand how to estimate and adjust the stringency of hybridization conditions such that sequences having at least a desired level of complementarity will stably hybridize, while those having lower complementarity will not. For examples of hybridization conditions and parameters, see, e.g., Sambrook, et al., 1989, *Molecular Cloning: A Laboratory Manual*, Second Edition, Cold Spring Harbor Press, Plainview, N.Y.; Ausubel, F. M. et al. 1994, *Current Protocols in Molecular Biology*, John Wiley & Sons, Secaucus, N.J. In some embodiments, specific hybridization occurs under stringent hybridization conditions. An oligonucleotide or polynucleotide (e.g., a probe or a primer) that is specific for a target nucleic acid will "hybridize" to the target nucleic acid under suitable conditions.

As used herein, the terms "individual", "patient", or "subject" can be an individual organism, a vertebrate, a mammal, or a human. In a preferred embodiment, the individual, patient or subject is a human.

As used herein, the term "library" refers to a collection of nucleic acid sequences, e.g., a collection of nucleic acids derived from whole genomic, subgenomic fragments, cDNA, cDNA fragments, RNA, RNA fragments, or a combination thereof. In one embodiment, a portion or all of the library nucleic acid sequences comprises an adapter sequence. The adapter sequence can be located at one or both ends. The adapter sequence can be useful, e.g., for a sequencing method (e.g., an NGS method), for amplification, for reverse transcription, or for cloning into a vector.

The library can comprise a collection of nucleic acid sequences, e.g., a target nucleic acid sequence (e.g., a tumor nucleic acid sequence), a reference nucleic acid sequence, or a combination thereof). In some embodiments, the nucleic acid sequences of the library can be derived from a single subject. In other embodiments, a library can comprise nucleic acid sequences from more than one subject (e.g., 2, 3, 4, 5, 6, 7, 8, 9, 10, 20, 30 or more subjects). In some embodiments, two or more libraries from different subjects can be combined to form a library having nucleic acid sequences from more than one subject. In one embodiment, the subject is human having, or at risk of having, a hereditary cancer.

A "library nucleic acid sequence" refers to a nucleic acid molecule, e.g., a DNA, RNA, or a combination thereof, that is a member of a library. Typically, a library nucleic acid sequence is a DNA molecule, e.g., genomic DNA or cDNA. In some embodiments, a library nucleic acid sequence is fragmented, e.g., sheared or enzymatically prepared, genomic DNA. In certain embodiments, the library nucleic acid sequences comprise sequence from a subject and sequence not derived from the subject, e.g., adapter sequence, a primer sequence, or other sequences that allow for identification, e.g., "barcode" sequences.

"Next generation sequencing or NGS" as used herein, refers to any sequencing method that determines the nucleotide sequence of either individual nucleic acid molecules (e.g., in single molecule sequencing) or clonally expanded proxies for individual nucleic acid molecules in a high throughput parallel fashion (e.g., greater than $10^3$, $10^4$, $10^5$ or more molecules are sequenced simultaneously). In one embodiment, the relative abundance of the nucleic acid species in the library can be estimated by counting the relative number of occurrences of their cognate sequences in the data generated by the sequencing experiment. Next generation sequencing methods are known in the art, and are described, e.g., in Metzker, M. *Nature Biotechnology Reviews* 11:31-46 (2010).

As used herein, "oligonucleotide" refers to a molecule that has a sequence of nucleic acid bases on a backbone comprised mainly of identical monomer units at defined intervals. The bases are arranged on the backbone in such a way that they can bind with a nucleic acid having a sequence of bases that are complementary to the bases of the oligonucleotide. The most common oligonucleotides have a backbone of sugar phosphate units. A distinction may be made between oligodeoxyribonucleotides that do not have a hydroxyl group at the 2' position and oligoribonucleotides that have a hydroxyl group at the 2' position. Oligonucleotides may also include derivatives, in which the hydrogen of the hydroxyl group is replaced with organic groups, e.g., an allyl group. Oligonucleotides that function as primers or probes are generally at least about 10-15 nucleotides in length or up to about 70, 100, 110, 150 or 200 nucleotides in length, and more preferably at least about 15 to 25 nucleotides in length. Oligonucleotides used as primers or probes for specifically amplifying or specifically detecting a particular target nucleic acid generally are capable of specifically hybridizing to the target nucleic acid.

As used herein, the term "primer" refers to an oligonucleotide, which is capable of acting as a point of initiation of nucleic acid sequence synthesis when placed under conditions in which synthesis of a primer extension product which is complementary to a target nucleic acid strand is induced, i.e., in the presence of different nucleotide triphosphates and a polymerase in an appropriate buffer ("buffer" includes pH, ionic strength, cofactors etc.) and at a suitable temperature. One or more of the nucleotides of the primer can be modified for instance by addition of a methyl group, a biotin or digoxigenin moiety, a fluorescent tag or by using radioactive nucleotides. A primer sequence need not reflect the exact sequence of the template. For example, a non-complementary nucleotide fragment may be attached to the 5' end of the primer, with the remainder of the primer sequence being substantially complementary to the strand. The term primer as used herein includes all forms of primers that may be synthesized including peptide nucleic acid primers, locked nucleic acid primers, phosphorothioate modified primers, labeled primers, and the like. The term "forward primer" as used herein means a primer that anneals to the anti-sense strand of double-stranded DNA (dsDNA). A "reverse primer" anneals to the sense-strand of dsDNA.

Primers are typically at least 10, 15, 18, or 30 nucleotides in length or up to about 100, 110, 125, or 200 nucleotides in length. In some embodiments, primers are preferably between about 15 to about 60 nucleotides in length, and most preferably between about 25 to about 40 nucleotides in length. In some embodiments, primers are 15 to 35 nucleotides in length. There is no standard length for optimal hybridization or polymerase chain reaction amplification. An optimal length for a particular primer application may be readily determined in the manner described in H. Erlich, *PCR Technology*, PRINCIPLES AND APPLICATION FOR DNA AMPLIFICATION, (1989).

As used herein, the term "primer pair" refers to a forward and reverse primer pair (i.e., a left and right primer pair) that can be used together to amplify a given region of a nucleic acid of interest.

"Probe" as used herein refers to nucleic acid that interacts with a target nucleic acid via hybridization. A probe may be fully complementary to a target nucleic acid sequence or partially complementary. The level of complementarity will depend on many factors based, in general, on the function of the probe. Probes can be labeled or unlabeled, or modified in any of a number of ways well known in the art. A probe may specifically hybridize to a target nucleic acid. Probes may be DNA, RNA or a RNA/DNA hybrid. Probes may be oligonucleotides, artificial chromosomes, fragmented artificial chromosome, genomic nucleic acid, fragmented genomic nucleic acid, RNA, recombinant nucleic acid, fragmented recombinant nucleic acid, peptide nucleic acid (PNA), locked nucleic acid, oligomer of cyclic heterocycles, or conjugates of nucleic acid. Probes may comprise modified nucleobases, modified sugar moieties, and modified internucleotide linkages. Probes are typically at least about 10, 15, 20, 25, 30, 35, 40, 50, 60, 75, 100 nucleotides or more in length.

As used herein, the term "sample" refers to clinical samples obtained from a patient. In preferred embodiments, a sample is obtained from a biological source (i.e., a "biological sample"), such as tissue or bodily fluid collected from a subject. Sample sources include, but are not limited to, mucus, sputum (processed or unprocessed), bronchial alveolar lavage (BAL), bronchial wash (BW), blood, bodily fluids, cerebrospinal fluid (CSF), urine, plasma, serum, or tissue (e.g., biopsy material). Preferred sample sources include plasma, serum, or whole blood.

The term "sensitivity," as used herein in reference to the methods of the present technology, is a measure of the ability of a method to detect a preselected sequence variant in a heterogeneous population of sequences. A method has a sensitivity of S % for variants of F if, given a sample in which the preselected sequence variant is present as at least F % of the sequences in the sample, the method can detect the preselected sequence at a preselected confidence of C %, S % of the time. By way of example, a method has a sensitivity of 90% for variants of 5% if, given a sample in which the preselected variant sequence is present as at least 5% of the sequences in the sample, the method can detect the preselected sequence at a preselected confidence of 99%, 9 out of 10 times (F=5%; C=99%; S=90%). Exemplary sensitivities include at least 50, 60, 70, 80, 90, 95, 98, and 99%.

The term "specific" as used herein in reference to an oligonucleotide primer means that the nucleotide sequence of the primer has at least 12 bases of sequence identity with a portion of the nucleic acid to be amplified when the oligonucleotide and the nucleic acid are aligned. An oligonucleotide primer that is specific for a nucleic acid is one that, under the stringent hybridization or washing conditions, is capable of hybridizing to the target of interest and not substantially hybridizing to nucleic acids which are not of interest. Higher levels of sequence identity are preferred and include at least 75%, at least 80%, at least 85%, at least 90%, at least 85-95% and more preferably at least 98% sequence identity. Sequence identity can be determined using a commercially available computer program with a default setting that employs algorithms well known in the art. As used herein, sequences that have "high sequence identity" have identical nucleotides at least at about 50% of aligned nucleotide positions, preferably at least at about 60% of aligned nucleotide positions, and more preferably at least at about 75% of aligned nucleotide positions.

"Specificity," as used herein, is a measure of the ability of a method to distinguish a truly occurring preselected sequence variant from sequencing artifacts or other closely related sequences. It is the ability to avoid false positive detections. False positive detections can arise from errors introduced into the sequence of interest during sample preparation, sequencing error, or inadvertent sequencing of closely related sequences like pseudo-genes or members of a gene family. A method has a specificity of X % if, when applied to a sample set of $N_{Total}$ sequences, in which $X_{True}$ sequences are truly variant and $X_{Not\ true}$ are not truly variant, the method selects at least X % of the not truly variant as not variant. E.g., a method has a specificity of 90% if, when applied to a sample set of 1,000 sequences, in which 500 sequences are truly variant and 500 are not truly variant, the method selects 90% of the 500 not truly variant sequences as not variant. Exemplary specificities include at least 50, 60, 70, 80, 90, 95, 98, and 99%.

The term "stringent hybridization conditions" as used herein refers to hybridization conditions at least as stringent as the following: hybridization in 50% formamide, 5×SSC, 50 mM $NaH_2PO4$, pH 6.8, 0.5% SDS, 0.1 mg/mL sonicated salmon sperm DNA, and 5×Denhart's solution at 42° C. overnight; washing with 2×SSC, 0.1% SDS at 45° C.; and washing with 0.2×SSC, 0.1% SDS at 45° C. In another example, stringent hybridization conditions should not allow for hybridization of two nucleic acids which differ over a stretch of 20 contiguous nucleotides by more than two bases.

The terms "target nucleic acid" or "target sequence" as used herein refer to a nucleic acid sequence of interest to be detected and/or quantified in the sample to be analyzed. Target nucleic acid may be composed of segments of a chromosome, a complete gene with or without intergenic sequence, segments or portions of a gene with or without intergenic sequence, or sequence of nucleic acids which probes or primers are designed. Target nucleic acids may include a wild-type sequence(s), a mutation, deletion, insertion or duplication, tandem repeat elements, a gene of interest, a region of a gene of interest or any upstream or downstream region thereof. Target nucleic acids may represent alternative sequences or alleles of a particular gene. Target nucleic acids may be derived from genomic DNA, cDNA, or RNA.

As used herein, the terms "treat," "treating" or "treatment" refer, to an action to obtain a beneficial or desired clinical result including, but not limited to, alleviation or amelioration of one or more signs or symptoms of a disease or condition (e.g., regression, partial or complete), diminishing the extent of disease, stability (i.e., not worsening, achieving stable disease) state of disease, amelioration or palliation of the disease state, diminishing rate of or time to progression, and remission (whether partial or total).

Microsampling Devices Employed in the Methods of the Present Technology

Conventional dried blood spotting techniques are accompanied by a number of drawbacks, including imprecise sample volume and reliance on a constant sample viscosity (i.e., the expectation that the sample will spread uniformly on the sample card). A constant viscosity results in blood spot diameters remaining constant when equal volume samples are administered to the cards. However, viscosity varies significantly between blood samples because of differing hematocrit (HCT) or packed cell volume (PCV) levels in the blood. Samples with high hematocrit levels form smaller diameter spots on the bloodspot papers, leading to different concentrations of blood within the fixed diameter of the spots sampled. PCV levels are believed to show a variance of about 45% in spot diameters. As internal standards are sprayed onto the spotted blood, this can result in a 45% error in quantitation. The microsampling devices employed in the methods disclosed herein confer several advantages, including the collection of more precise blood volumes, lack of hematocrit bias, and the ability to be easily automated with standard liquid handlers for lab processing.

Additionally, conventional blood spot techniques require a comparatively large volume of blood relative to the disclosed microsampling devices. A dried blood spot would generally require 50-75 µl per spot, while a microsampling device can yield results from approximately 20 µl. It has been recognized in the art that dried blood spots often have performance variability issues for detecting viral load compared to other samples types, such as plasma (Pannus et al., *Medicine*, 95:48(e5475) (2016)), and the volume of a dried blood spot may need to be significantly higher for certain types of assessment (e.g., optical density) compared to other sample types, such as serum (Brandao et al., *J. Clin. Virol.*, 57:98-102 (2013)). Indeed, found that using both dried blood spot and plasma spot screening for detecting viral load and treatment failure in HIV patients receiving antiretroviral therapy found that both yielded a high rate of false positives (Sawadogo et al., J. Clin. Microbiol., 52(11):3878-83 (2014)).

The microsampling device useful in the methods of the present technology comprises an absorbent tip having a distal end and a proximal end. The width of the distal end of the absorbent tip is narrow compared to the width of the proximal end. The proximal end is attached to a holder, whereas the distal end is configured to contact a fluid to be absorbed, such as blood. The microsampling device permits biological fluid samples, such as blood, to be easily dried, shipped, and then later analyzed. In certain embodiments, the biological fluid is blood from a fingerstick.

Wicking action draws the blood into the absorbent tip. An optional barrier between the absorbent tip and the holder prevents blood from passing or wicking to the holder. The absorbent tip is composed of a material that wicks up substantially the same volume of fluid even when excess fluid is available (volumetric absorptive microsampling or VAMS™). The volume of the absorbent tip affects the volume of fluid absorbed. The size and shape of the absorbent tip may be varied to adjust the volume of absorbed blood and the rate of absorption. Blood volumes of about 7-15 µL, about 20 µL and even up to about 30 µL may be acceptable. The sampling time may be about 2 seconds, about 3 seconds, about 5 seconds, or up to about 10 seconds.

In some embodiments, the material used for the absorbent tip is hydrophilic (e.g., polyester). Alternatively, the material may initially be hydrophobic and is subsequently treated to make it hydrophilic. Hydrophobic matrices may be rendered hydrophilic by a variety of known methods, such as plasma treatment or surfactant treatment (e.g., Tween-40 or Tween-80) of the matrix. In some embodiments, plasma treatment is used to render a hydrophobic material such as polyolefin, e.g., polyethylene, hydrophilic. Alternatively, the grafting of hydrophilic polymers to the surface and the chemical functionalization of active groups on the surface with polar or hydrophilic molecules such as sugars can be used to achieve a hydrophilic surface for the absorbent tip. Covalent modification could also be used to add polar or hydrophilic functional groups to the surface of absorbent tip. Other suitable materials for the absorbent tip include sintered glass, sintered steel, sintered ceramics, and sintered polymers of plastic, and sintered polyethylene.

In some embodiments, the microsampling device comprises an absorbent tip made of a hydrophilic polymeric material of sufficient size to absorb a maximum of about 20 µL of blood in about 2-5 seconds, and having a length of less than about 5 mm (0.2 inches) and a cross-sectional area of less than about 20 mm$^2$ and a density of less than about 4 g/cc. In some embodiments, the absorbent tips are composed of polyethylene and configured to absorb about 1-20 microliters of blood, preferably within 1-7 seconds, and more preferably within about 1-5 seconds. The absorbent tip may contain one or more of dried blood, dried anticoagulant or an internal standard.

In certain embodiments, the absorbent tips have a volume of about 35 mm$^3$, absorb about 13-14 microliters of blood in about 3 seconds, absorb 9-10 microliters of blood in about 2.5 seconds, and have a pore volume of about 38%. In other embodiments, the absorbent tips have a volume of about 24 microliters, a density of about 0.6 g/cc, absorb about 10 microliters of blood in about 2.5 seconds, and have a pore volume of about 40%. In some embodiments, the volumetric absorptive microsampling device is a MITRA® tip, as described in US 2013/0116597, which is herein incorporated by reference in its entirety.

The absorbent tip may be shaped with an exterior resembling a truncated cone with a narrow and rounded distal end. In some embodiments, the holder has a cylindrical post that fits into a recess inside the center of the absorbent tip and extending along the longitudinal axis of the absorbent tip and holder. The conical shape of the absorbent tip helps wick the sample quickly and uniformly.

The holder may be adapted for use with a pipette. In some embodiments, a tubular, conical shaped holder is preferred, with the absorbent tip on the narrow end of the holder. The wider opposite end of the holder may be closed, or open and hollow, and may optionally be configured to attach to a pipette tip. The holder may have outwardly extending flanges that are arranged to abut mating structures in holders, drying racks or test equipment to help position the absorbent tip at desired locations in such holders, drying racks and test equipment.

In certain embodiments, the holder may include a pipette tip or a tapering, tubular structure configured to nest with a pipette tip. The absorbent tip may be composed of polyethylene, and both the absorbent tip and holder are made under aseptic conditions, or are terminally sterilized. The absorbent tip may contain dried anti-coagulant. In some embodiments, the holder has a plurality of ribs extending along a length of the holder. The ribs may have a height and length selected to keep the absorbent tip from contacting walls of a recess into which the holder and absorbent tip are placed for shipment, or for extraction of the dried blood in the absorbent tip.

After absorbing a small-volume sample, the absorbent tip is then dried. In some embodiments, the small-volume blood sample is dried for at least 10 minutes, at least 20 minutes, at least 30 minutes, at least 40 minutes, at least 50 minutes, at least 1 hour, at least 2 hours, at least 3 hours, at least 4 hours, at least 5 hours, at least 6 hours, at least 8 hours, at least 12 hours, at least 16 hours, at least 20 hours, at least 24 hours, at least 48 hours, at least 72 hours, or at least 96 hours at ambient or room temperature. In certain embodiments, the small-volume blood sample is dried for about 2-3 hours.

Drying can be done on a suitable rack or holder, or preferably the absorbent tip and holder can be transferred to a special drying container configured to facilitate drying while minimizing contact between the absorbent tip and the walls of the drying container or other potential contaminant surfaces. The drying container may have a desiccant to facilitate drying. The drying container may also provide a protective cover which may be sealed for transport to prevent contamination. In some embodiments, the cover has a surface onto which printed indicia may be written to identify the source of the dried blood sample and provide other relevant information. In some embodiments, the dimensions of the container, and the relative positions of the holders within the container, will conform to SBS Microwell plate specifications. The microsampling device and the drying container may be placed in a plastic bag along with a desiccant to assist with drying and can either be shipped in this fashion, or shipped after the desiccant is removed.

In some embodiments, the wider opposite end of the holder is hollow and the container has a first portion with a mounting projection portion sized to fit into and releasably engage the hollow end of the holder. Additionally or alternatively, the container has a second portion releasably fastened to the first portion and has a recess configured to enclose a portion of the holder for transportation of the holder. The container may comprise a plurality of openings allowing air to access the absorbent tip of the microsampling device. Moreover, the first portion may have a side with an access port therein of sufficient size and located so that indicia may be applied through the port and onto the holder when the holder is on the mounting projection.

Upon receipt at the testing location, the absorbent tip may be eluted in a predetermined volume of a suitable buffer (as described herein) either manually or via automated means to extract the nucleic acids or proteins of interest from dried blood. Physical agitation techniques such as sonication or vortexing of the fluid and/or the absorbent tip may accelerate the extraction process from the dried blood into a liquid sample matrix. Physical separation techniques such as centrifugation, evaporation/reconstitution, concentration, precipitation, liquid/liquid extraction, and solid phase extraction can be used to further simplify the sample matrix for further analysis.

Each container may enclose a plurality of holders, wherein each holder comprises an absorbent tip at its distal end and has a hollow proximal end. The container likewise has a plurality of elongated mounting projections each sized to fit into and releasably engage the hollow ends of the plurality of holders. The second portion of the container has recesses configured to separately enclose each of the plurality of holders in a separate enclosure within the container. In certain embodiments, each of the plurality of holders has a plurality of ribs extending along a length of the holder with the ribs configured to keep the absorbent tip from contacting walls of the container. As desired, a desiccant may be placed inside the container to help dry the blood in the absorbent tip or maintain dryness. Each holder may have visible indicia associating the holder with the container and with at least one other holder, such as serial numbers with various portions of the number indicating related holders/absorbent tips and the container in which the holders are shipped.

Nucleic Acid Extraction

In one aspect, the present disclosure provides a method for extracting genomic DNA from a dried biological fluid sample collected with a volumetric absorptive microsampling device (e.g., MITRA® Tip). In some embodiments, the dried biological fluid sample is eluted by contacting the absorbent tip of a volumetric absorptive microsampling device with a lysis buffer and proteinase K. The lysis buffer may comprise guanidine hydrochloride, Tris.Cl, EDTA, Tween 20, and Triton X-100. Proteinase K is a broad spectrum serine protease that is stable over a wide pH range (4-12), with a pH optimum of pH 8.0. The predominant site of Proteinase K cleavage is the peptide bond adjacent to the carboxyl group of aliphatic and aromatic amino acids with blocked alpha amino groups. Elevating the reaction temperature from 37° C. to 50-60° C. may increase the Proteinase K activity by several fold. Proteinase K activity can be enhanced by the addition of 0.5-1% sodium dodecyl sulfate (SDS), 3 M Guanidinium chloride, 1 M Guanidinium thiocyanate, or 4 M urea.

Alternatively, other protocols for nucleic acid extraction may be used in the methods of the present technology. Examples of other commercially available nucleic acid purification kits include Molzym GmbH & Co KG (Bremen, DE), Qiagen (Hilden, DE), Macherey-Nagel (Duren, DE), Roche (Basel, CH) or Sigma (Deisenhofen, DE). Other systems for nucleic acid purification, which are based on the use of polystyrene beads etc., as support material may also be used.

In some embodiments, extraction of genomic DNA from a dried biological fluid sample collected with a volumetric absorptive microsampling device comprises denaturing nucleoprotein complexes in cells present in the dried biological fluid sample. In certain embodiments, extraction of genomic DNA from a dried biological fluid sample collected with a volumetric absorptive microsampling device comprises removing protein contaminants, inactivating nuclease activity, and/or removing biological and/or chemical contaminants present in the dried biological fluid sample.

In some embodiments, extraction of genomic DNA from a dried biological fluid sample collected with a volumetric absorptive microsampling device may be performed using automated DNA extraction platforms. In some embodiments, the automated DNA extraction platform has high-throughput capacity, such as up to 100 extractions per cycle. In certain embodiments, extraction of genomic DNA from a dried biological fluid sample collected with a volumetric absorptive microsampling device may be performed using commercially available automated workstations, such as the QIAsymphony® or Hamilton® automation. In some embodiments, extraction of genomic DNA from a dried biological fluid sample collected with a volumetric absorptive microsampling device is performed on a Biorobot® EZ1™ automated system. In some embodiments, extraction of genomic DNA from a dried biological fluid sample collected with a volumetric absorptive microsampling device is performed using commercially available reagent kits.

Multiplex Ligation-Dependent Probe Amplification (MLPA)

Multiplex ligation-dependent probe amplification (MLPA) is a variation of the multiplex polymerase chain reaction that permits amplification of multiple targets with only a single primer pair. The MLPA reaction can be divided in four major steps: 1) DNA denaturation and hybridization of MLPA hemi-probes; 2) ligation reaction; 3) PCR amplification; 4) separation of amplification products by electrophoresis. During the first step, the DNA is denatured and incubated overnight with a mixture of MLPA probes. Each MLPA probe consists of two oligonucleotides (or hemi-probes) which recognize adjacent target sites on the DNA. One hemi-probe oligonucleotide comprises a sequence recognized by the forward primer, while the other hemi-probe comprises a sequence recognized by the reverse primer. The hemi-probes are ligated into a complete probe only when both hemi-probe oligonucleotides are hybridized to their respective targets. The advantage of using hemi-probes is that only the ligated oligonucleotides, but not the unbound hemi-probe oligonucleotides, are amplified. Because only ligated probes will be exponentially amplified during the subsequent PCR reaction, the number of probe ligation products is a measure for the number of target sequences in the sample.

Each complete probe has a unique length, so that its resulting amplicons can be separated and identified by (capillary) electrophoresis. This feature avoids the resolution limitations of multiplex PCR. Because the forward primer used for probe amplification is detectably labeled, each amplicon generates a fluorescent peak which can be detected by a capillary sequencer. Comparing the peak pattern obtained on a given sample with that obtained on various reference samples, the relative quantity of each amplicon can be determined. This ratio is a measure for the ratio in which the target sequence is present in the sample DNA.

NGS Platforms

Following the production of an adapter tagged amplicon library, the amplicons are sequenced using high throughput, massively parallel sequencing (i.e., next generation sequencing). In some embodiments, high throughput, massively parallel sequencing employs sequencing-by-synthesis with reversible dye terminators. In other embodiments, sequencing is performed via sequencing-by-ligation. In other embodiments, sequencing is single molecule sequencing. Examples of Next Generation Sequencing techniques include, but are not limited to pyrosequencing, Reversible dye-terminator sequencing, SOLiD sequencing, Ion semiconductor sequencing, Helioscope single molecule sequencing etc.

The Ion Torrent™ (Life Technologies, Carlsbad, Calif.) amplicon sequencing system employs a flow-based approach that detects pH changes caused by the release of hydrogen ions during incorporation of unmodified nucleotides in DNA replication. For use with this system, a sequencing library is initially produced by generating DNA fragments flanked by sequencing adapters. In some embodiments, these fragments can be clonally amplified on particles by emulsion PCR. The particles with the amplified template are then placed in a silicon semiconductor sequencing chip. During replication, the chip is flooded with one nucleotide after another, and if a nucleotide complements the DNA molecule in a particular microwell of the chip, then it will be incorporated. A proton is naturally released when a nucleotide is incorporated by the polymerase in the DNA molecule, resulting in a detectable local change of pH. The pH of the solution then changes in that well and is detected by the ion sensor. If homopolymer repeats are present in the template sequence, multiple nucleotides will be incorporated in a single cycle. This leads to a corresponding number of released hydrogens and a proportionally higher electronic signal.

The 454™ GS FLX™ sequencing system (Roche, Germany), employs a light-based detection methodology in a large-scale parallel pyrosequencing system. Pyrosequencing uses DNA polymerization, adding one nucleotide species at a time and detecting and quantifying the number of nucleotides added to a given location through the light emitted by the release of attached pyrophosphates. For use with the 454™ system, adapter-ligated DNA fragments are fixed to small DNA-capture beads in a water-in-oil emulsion and amplified by PCR (emulsion PCR). Each DNA-bound bead is placed into a well on a picotiter plate and sequencing reagents are delivered across the wells of the plate. The four DNA nucleotides are added sequentially in a fixed order across the picotiter plate device during a sequencing run. During the nucleotide flow, millions of copies of DNA bound to each of the beads are sequenced in parallel. When a nucleotide complementary to the template strand is added to a well, the nucleotide is incorporated onto the existing DNA strand, generating a light signal that is recorded by a CCD camera in the instrument.

Sequencing technology based on reversible dye-terminators: DNA molecules are first attached to primers on a slide and amplified so that local clonal colonies are formed. Four types of reversible terminator bases (RT-bases) are added, and non-incorporated nucleotides are washed away. Unlike pyrosequencing, the DNA can only be extended one nucleotide at a time. A camera takes images of the fluorescently labeled nucleotides, then the dye along with the terminal 3' blocker is chemically removed from the DNA, allowing the next cycle.

Helicos Biosciences Corp's (Cambridge, Mass.) single-molecule sequencing uses DNA fragments with added polyA tail adapters, which are attached to the flow cell surface. At each cycle, DNA polymerase and a single species of fluorescently labeled nucleotide are added, resulting in template-dependent extension of the surface-immobilized primer-template duplexes. The reads are performed by the Helioscope sequencer. After acquisition of images tiling the full array, chemical cleavage and release of the fluorescent label permits the subsequent cycle of extension and imaging.

Sequencing by synthesis (SBS), like the "old style" dye-termination electrophoretic sequencing, relies on incorporation of nucleotides by a DNA polymerase to determine the base sequence. A DNA library with affixed adapters is denatured into single strands and grafted to a flow cell, followed by bridge amplification to form a high-density array of spots onto a glass chip. Reversible terminator methods use reversible versions of dye-terminators, adding one nucleotide at a time, detecting fluorescence at each position by repeated removal of the blocking group to allow polymerization of another nucleotide. The signal of nucleotide incorporation can vary with fluorescently labeled nucleotides, phosphate-driven light reactions and hydrogen ion sensing having all been used. Examples of SBS platforms include Illumina GA, HiSeq 2500, HiSeq 1500, HiSeq 2000, or HiSeq 1000. The MiSeq® personal sequencing system (Illumina, Inc.) also employs sequencing by synthesis with reversible terminator chemistry.

In contrast to the sequencing by synthesis method, the sequencing by ligation method uses a DNA ligase to determine the target sequence. This sequencing method relies on enzymatic ligation of oligonucleotides that are adjacent through local complementarity on a template DNA strand. This technology employs a partition of all possible oligonucleotides of a fixed length, labeled according to the sequenced position. Oligonucleotides are annealed and ligated and the preferential ligation by DNA ligase for matching sequences results in a dinucleotide encoded color space signal at that position (through the release of a fluorescently labeled probe that corresponds to a known nucleotide at a known position along the oligo). This method is primarily used by Life Technologies' SOLiD™ sequencers. Before sequencing, the DNA is amplified by emulsion PCR. The resulting beads, each containing only copies of the same DNA molecule, are deposited on a solid planar substrate.

SMRT™ sequencing is based on the sequencing by synthesis approach. The DNA is synthesized in zero-mode wave-guides (ZMWs)-small well-like containers with the capturing tools located at the bottom of the well. The sequencing is performed with use of unmodified polymerase (attached to the ZMW bottom) and fluorescently labeled nucleotides flowing freely in the solution. The wells are constructed in a way that only the fluorescence occurring at the bottom of the well is detected. The fluorescent label is detached from the nucleotide at its incorporation into the DNA strand, leaving an unmodified DNA strand.

High-throughput sequencing of DNA can also take place using AnyDot-chips (Genovoxx, Germany), which allows monitoring of biological processes (e.g., miRNA expression or allele variability (SNP detection)). For example, the AnyDot-chips allow for 10×-50× enhancement of nucleotide fluorescence signal detection. Other high-throughput sequencing systems include those disclosed in Venter, J., et al., Science 16 Feb. 2001; Adams, M. et al., Science 24 Mar. 2000; and M. J, Levene, et al., Science 299:682-686, January 2003; as well as U.S. Application Pub. No. 2003/0044781 and 2006/0078937.

Hereditary Cancer Detection Assays of the Present Technology

Provided herein are methods for detecting at least one mutation in a plurality of hereditary cancer-related genes in a dried biological fluid sample comprising isolating genomic DNA from a dried biological fluid sample eluted from an absorbent tip of a microsampling device (e.g., MITRA® Tip) with a lysis buffer and Proteinase K, wherein the plurality of hereditary cancer-related genes comprises APC, ATM, BARD1, BMPR1A, BRCA1, BRCA2, BRIP1, CDH1, CDK4, CDKN2A (p14ARF and p16), CHEK2, EPCAM, MEN1, MLH1, MSH2, MSH6, MUTYH, NBN, NF1, PALB2, PMS2, POLD1, POLE, PTEN, RAD51C, RAD51D, RET, SDHB, SDHC, SDHD, SMAD4, STK11, TP53, and VHL. In certain embodiments, the at least one mutation in the plurality of hereditary cancer-related genes is detected using high throughput massive parallel sequencing. In some embodiments, the lysis buffer comprises guanidine hydrochloride, Tris.Cl, EDTA, Tween 20, and Triton X-100.

In one aspect, the present technology provides a method for detecting at least one mutation in a plurality of hereditary cancer-related genes in a dried biological fluid sample comprising (a) extracting genomic DNA from a dried biological fluid sample eluted from an absorbent tip of a microsampling device; (b) generating a library comprising amplicons corresponding to each of the plurality of hereditary cancer-related genes, said plurality of hereditary cancer-related genes comprising APC, ATM, BARD1, BMPR1A, BRCA1, BRCA2, BRIP1, CDH1, CDK4, CDKN2A (p14ARF and p16), CHEK2, EPCAM MEN1, MLH1, MSH2, MSH6, MUTYH, NBN, NF1, PALB2, PMS2, POLD1, POLE, PTEN, RAD51C, RAD51D, RET, SDHB, SDHC, SDHD, SMAD4, STK11, TP53, and VHL, wherein an adapter sequence is ligated to the ends of the plurality of amplicons; and (c) detecting at least one mutation in at least one of the plurality of amplicons using high throughput massive parallel sequencing. In some embodiments, the dried biological fluid sample is dried plasma, dried serum, or dried whole blood. In certain embodiments, the dried biological fluid sample is obtained from a patient having, or is suspected of having a hereditary cancer. The hereditary cancer may be breast cancer, ovarian cancer, colon cancer, or skin cancer.

Additionally or alternatively, in some embodiments, the dried biological fluid sample on the absorbent tip of the microsampling device is collected from a patient via fingerstick. In certain embodiments, the microsampling device is a MITRA® tip. Elution of the dried biological fluid sample may be performed by contacting the absorbent tip of the microsampling device with a lysis buffer and Proteinase K. In certain embodiments, the lysis buffer comprises guanidine hydrochloride, Tris.Cl, EDTA, Tween 20, and Triton X-100. In a further embodiment, the lysis buffer comprises 800 mM guanidine hydrochloride; 30 mM Tris.Cl, pH 8.0; 30 mM EDTA, pH 8.0; 5% Tween 20; and 0.5% Triton X-100.

Additionally or alternatively, in some embodiments, elution of the dried biological fluid sample is performed by contacting the absorbent tip of the microsampling device with the lysis buffer for up to 15 minutes at 90° C. Additionally or alternatively, in certain embodiments, elution of the dried biological fluid sample is performed by contacting the absorbent tip of the microsampling device with Proteinase K for up to 1 hour at 56° C. In other embodiments, elution of the dried biological fluid sample is performed by contacting the absorbent tip of the microsampling device with Proteinase K for up to 16-18 hours at 56° C. In some embodiments, the sample volume of the microsampling device is no more than 10-20 µL.

In some embodiments of the method, no more than 400 ng of genomic DNA is eluted from the absorbent tip of the microsampling device. In other embodiments of the method, about 100 ng to about 400 ng of genomic DNA is eluted from the absorbent tip of the microsampling device.

Additionally or alternatively, in some embodiments, the plurality of amplicons further comprises a unique index sequence. In certain embodiments, the plurality of amplicons are enriched using a bait set comprising nucleic acid sequences that are complementary to at least one of the plurality of amplicons. In some embodiments, the nucleic acid sequences of the bait set are RNA baits, DNA baits, or a combination thereof.

In one embodiment, the methods featured in the present technology are used in a multiplex, multi-gene assay format, e.g., assays that incorporate multiple signals from a large number of diverse genetic alterations in a large number of genes.

In some embodiments of the method, the at least one mutation detected is a mutation in APC, ATM, BARD1, BMPR1A, BRCA1, BRCA2, BRIP1, CDH1, CDK4, CDKN2A (p14ARF and p16), CHEK2, EPCAM, MEN1, MLH1, MSH2, MSH6, MUTYH, NBN, NF1, PALB2, PMS2, POLD1, POLE, PTEN, RAD51C, RAD51D, RET, SDHB, SDHC, SDHD, SMAD4, STK11, TP53, and VHL.

In some embodiments, a single primer or one or both primers of a primer pair comprise a specific adapter sequence (also referred to as a sequencing adapter) ligated to the 5' end of the target specific sequence portion of the primer. This sequencing adapter is a short oligonucleotide of known sequence that can provide a priming site for both amplification and sequencing of the adjoining, unknown target nucleic acid. As such, adapters allow binding of a fragment to a flow cell for next generation sequencing. Any adapter sequence may be included in a primer used in the present technology. In certain embodiments, amplicons corresponding to specific regions of APC, ATM, BARD1, BMPR1A, BRCA1, BRCA2, BRIP1, CDH1, CDK4, CDKN2A (p14ARF and p16), CHEK2, EPCAM, MEN1, MLH1, MSH2, MSH6, MUTYH, NBN, NF1, PALB2, PMS2, POLD1, POLE, PTEN, RAD51C, RAD51D, RET, SDHB, SDHC, SDHD, SMAD4, STK11, TP53, and VHL are amplified using primers that contain an oligonucleotide sequencing adapter to produce adapter tagged amplicons.

In other embodiments, the employed primers do not contain adapter sequences and the amplicons produced are subsequently (i.e. after amplification) ligated to an oligonucleotide sequencing adapter on one or both ends of the amplicons. In some embodiments, all forward amplicons (i.e., amplicons extended from forward primers that hybridized with antisense strands of a target nucleic acid) contain the same adapter sequence. In some embodiments when double stranded sequencing is performed, all forward amplicons contain the same adapter sequence and all reverse amplicons (i.e., amplicons extended from reverse primers that hybridized with sense strands of a target segment) contain an adapter sequence that is different from the adapter sequence of the forward amplicons. In some embodiments, the adapter sequences further comprise an index sequence (also referred to as an index tag, a "barcode" or a multiplex identifier (MID)).

In some embodiments, the adapter sequences are P5 and/or P7 adapter sequences that are recommended for Illumina sequencers (MiSeq and HiSeq). See, e.g., Williams-Carrier et al., Plant J., 63(1):167-77 (2010). In some embodiments, the adapter sequences are P1, A, or Ion Xpress™ barcode adapter sequences that are recommended for Life Technologies sequencers. Other adapter sequences are known in the art. Some manufacturers recommend specific adapter sequences for use with the particular sequencing technology and machinery that they offer.

Additionally or alternatively, in some embodiments of the above methods, amplicons corresponding to specific regions of APC, ATM, BARD1, BMPR1A, BRCA1, BRCA2, BRIP1, CDH1, CDK4, CDKN2A (p14ARF and p16), CHEK2, EPCAM, MEN1, MLH1, MSH2, MSH6, MUTYH, NBN, NF1, PALB2, PMS2, POLD1, POLE, PTEN, RAD51C, RAD51D, RET, SDHB, SDHC, SDHD, SMAD4, STK11, TP53, and VHL from more than one sample are sequenced. In some embodiments, all samples are sequenced simultaneously in parallel.

In some embodiments of the above methods, amplicons corresponding to specific regions of APC, ATM, BARD1, BMPR1A, BRCA1, BRCA2, BRIP1, CDH1, CDK4, CDKN2A (p14ARF and p16), CHEK2, EPCAM, MEN1, MLH1, MSH2, MSH6, MUTYH, NBN, NF1, PALB2, PMS2, POLD1, POLE, PTEN, RAD51C, RAD51D, RET, SDHB, SDHC, SDHD, SMAD4, STK11, TP53, and VHL from at least 1, 5, 10, 20, 30 or up to 35, 40, 45, 48 or 50 different samples are amplified and sequenced using the methods described herein.

Additionally or alternatively, in some embodiments of the method, amplicons derived from a single sample may further comprise an identical index sequence that indicates the source from which the amplicon is generated, the index sequence for each sample being different from the index sequences from all other samples. As such, the use of index sequences permits multiple samples to be pooled per sequencing run and the sample source subsequently ascertained based on the index sequence. In some embodiments, the Access Array™ System (Fluidigm Corp., San Francisco, Calif.) or the Apollo 324 System (Wafergen Biosystems, Fremont, Calif.) is used to generate a barcoded (indexed) amplicon library by simultaneously amplifying the nucleic acids from the samples in one set up.

In some embodiments, indexed amplicons are generated using primers (for example, forward primers and/or reverse primers) containing the index sequence. Such indexed primers may be included during library preparation as a "barcoding" tool to identify specific amplicons as originating from a particular sample source. When adapter-ligated and/or indexed primers are employed, the adapter sequence and/or index sequence gets incorporated into the amplicon (along with the target-specific primer sequence) during amplification. Therefore, the resulting amplicons are sequencing-competent and do not require the traditional library preparation protocol. Moreover, the presence of the index tag permits the differentiation of sequences from multiple sample sources.

In some embodiments, the amplicons may be amplified with non-adapter-ligated and/or non-indexed primers and a sequencing adapter and/or an index sequence may be subsequently ligated to one or both ends of each of the resulting amplicons. In some embodiments, the amplicon library is generated using a multiplexed PCR approach.

Indexed amplicons from more than one sample source are quantified individually and then pooled prior to high throughput sequencing. As such, the use of index sequences permits multiple samples (i.e., samples from more than one sample source) to be pooled per sequencing run and the sample source subsequently ascertained based on the index sequence. "Multiplexing" is the pooling of multiple adapter-tagged and indexed libraries into a single sequencing run. When indexed primer sets are used, this capability can be exploited for comparative studies. In some embodiments, amplicon libraries from up to 48 separate sources are pooled prior to sequencing.

Following the production of an adapter tagged and, optionally indexed, amplicon library, the amplicons are sequenced using high throughput, massively parallel sequencing (i.e., next generation sequencing). Methods for performing high throughput, massively parallel sequencing are known in the art. In some embodiments of the method, the high throughput massive parallel sequencing is performed using 454™ GS FLX™ pyrosequencing, reversible dye-terminator sequencing, SOLiD sequencing, Ion semiconductor sequencing, Helioscope single molecule sequencing, sequencing by synthesis, sequencing by ligation, or SMRT™ sequencing. In some embodiments, high throughput massively parallel sequencing may be performed using a read depth approach.

Treatment for Hereditary Cancers

Disclosed herein are methods for determining whether a patient will benefit from treatment with one or more anti-cancer therapeutic agents.

Examples of breast and ovarian cancer therapies are well known in the art and include surgery, radiation therapy, hormonal therapy, chemotherapy, immunotherapy or combinations thereof. Immunotherapeutic agents include antibodies, radioimmunoconjugates and immunocytokines.

Classes of chemotherapeutic agents can include alkylating agents, platinum agents, taxanes, vinca agents, anti-estrogen drugs, aromatase inhibitors, ovarian suppression agents, VEGF/VEGFR inhibitors, EGF/EGFR inhibitors, PARP inhibitors, cytostatic alkaloids, cytotoxic antibiotics, antimetabolites, endocrine/hormonal agents, bisphosphonate therapy agents and targeted biological therapy agents (e.g., therapeutic peptides described in U.S. Pat. No. 6,306,832, WO 2012007137, WO 2005000889, WO 2010096603 etc.).

Specific chemotherapeutic agents include, but are not limited to, cyclophosphamide, fluorouracil (or 5-fluorouracil or 5-FU), methotrexate, edatrexate (10-ethyl-10-deaza-aminopterin), thiotepa, carboplatin, cisplatin, taxanes, paclitaxel, protein-bound paclitaxel, docetaxel, vinorelbine, tamoxifen, raloxifene, toremifene, fulvestrant, gemcitabine, irinotecan, ixabepilone, temozolmide, topotecan, vincristine, vinblastine, eribulin, mutamycin, capecitabine, anastrozole, exemestane, letrozole, leuprolide, abarelix, buserlin, goserelin, megestrol acetate, risedronate, pamidronate, ibandronate, alendronate, denosumab, zoledronate, trastuzumab, tykerb, anthracyclines (e.g., daunorubicin and doxorubicin), bevacizumab, or combinations thereof.

Combinational chemotherapeutic therapies can include AT: Adriamycin® (Doxorubicin) and Taxotere® (Docetaxel); AC: Adriamycin®, Cytoxan® (Cyclophosphamide); AC+Taxol®; AC+Taxotere®; CMF: Cytoxan®, Methotrexate, 5-fluorouracil; CEF: Cytoxan®, Ellence® (Epirubicin), and fluorouracil; EC: Ellence®, Cytoxan®; FAC: 5-fluorouracil, Adriamycin®, and Cytoxan®; GET: Gemzar® (Gemcitabine), Ellence®, and Taxol®; TC: Taxotere®, Cytoxan®; TC: Taxotere®, Paraplatin® (Carboplatin); TAC: Taxotere®, Adriamycin®, Cytoxan® or TCH: Taxotere®, Herceptin® (Trastuzumab), and Paraplatin®. Additional combination chemotherapeutic therapies for metastatic breast or ovarian cancer include: Taxol and Xeloda® (Capecitabine); Taxotere and Xeloda®; Taxotere and Paraplatin®; Taxol® and Paraplatin®; Taxol® and Gemzar®; Abraxane® (Protein-bound Paclitaxel) and Xeloda®; Abraxane® and Paraplatin®; Camptosor® (Irinotecan) and Temodar® (Temozolomide); Gemzar® and Paraplatin® or Ixempra® (Ixabepilone) and Xeloda®. In some embodiments, the chemotherapeutic agents include cyclophosphamide and 5-fluorouracil or include methotrexate, cyclophosphamide and 5-fluorouracil.

Non-limiting examples of anti-cancer drugs for treating skin cancer include aldesleukin, cobimetinib, dabrafenib, dacarbazine, fluorouracil, talimogene laherparepvec, imiquimod, recombinant Interferon Alfa-2b, ipilimumab, pembrolizumab, trametinib, nivolumab, peginterferon Alfa-2b, sonidegib, vismodegib, and vemurafenib.

Non-limiting examples of anti-cancer drugs for treating colon cancer include bevacizumab, capecitabine, cetuximab, irinotecan hydrochloride, leucovorin calcium, trifluridine and tipiracil hydrochloride, oxaliplatin, panitumumab, ramucirumab, regorafenib, and ziv-aflibercept.

In one aspect, the present disclosure provides a method for selecting a patient exhibiting cancer symptoms, or a patient at risk for hereditary cancer, for treatment with an anti-cancer therapeutic agent comprising (a) eluting a dried blood sample under conditions that result in the release of genomic DNA from blood cells, wherein the dried blood sample is collected from the patient with a volumetric absorptive microsampling device; (b) isolating genomic DNA from the eluted dried blood sample; (c) generating a library comprising amplicons corresponding to each of a plurality of hereditary cancer-related genes comprising APC, ATM, BARD1, BMPR1A, BRCA1, BRCA2, BRIP1, CDH1, CDK4, CDKN2A (p14ARF and p16), CHEK2, EPCAM, MEN1, MLH1, MSH2, MSH6, MUTYH, NBN, NF1, PALB2, PMS2, POLD1, POLE, PTEN, RAD51C, RAD51D, RET, SDHB, SDHC, SDHD, SMAD4, STK11, TP53, and VHL, wherein an adapter sequence is ligated to the ends of the plurality of amplicons; (d) detecting at least one mutation in at least one of the plurality of amplicons using high throughput massive parallel sequencing; and (e) selecting the patient for treatment with an anti-cancer therapeutic agent, if a mutation in at least one of the plurality of amplicons corresponding to one or more of APC, ATM, BARD1, BMPR1A, BRCA1, BRCA2, BRIP1, CDH1, CDK4, CDKN2A (p14ARF and p16), CHEK2, EPCAM, MEN1, MLH1, MSH2, MSH6, MUTYH, NBN, NF1, PALB2, PMS2, POLD1, POLE, PTEN, RAD51C, RAD51D, RET, SDHB, SDHC, SDHD, SMAD4, STK11, TP53, and VHL is detected. In certain embodiments, the volumetric absorptive microsampling device is a MITRA® tip. In some embodiments, the patient has, or is at risk for a hereditary cancer selected from the group consisting of breast cancer, ovarian cancer, skin cancer, or colon cancer.

Patients at risk for hereditary cancer include subjects having: (a) two or more close relatives diagnosed with cancer; (b) multiple primary tumors; (c) bilateral or rare cancers; (d) familial incidences of cancer in multiple generations; (e) a constellation of tumors consistent with a specific cancer syndrome; (f) certain ethnic backgrounds (e.g., Ashkenazi Jewish ancestry); or cancers that manifest at a young age.

Cancer symptoms include, but are not limited to, persistent cough or blood-tinged saliva, change in bowel habits, bloody stool, anemia, breast lumps or breast discharge, testicular lumps, change in urination frequency, hematuria, hoarseness, persistent lumps or swollen glands, moles that bleed or have irregular edges, indigestion or difficulty swallowing, unusual vaginal bleeding or discharge, unexpected weight loss, night sweats, fever, persistent itching in the anal or genital area, non-healing sores, headaches, back pain, pelvic pain, and bloating.

In any of the above embodiments, the anti-cancer therapeutic agent is one or more agents selected from the group consisting of cyclophosphamide, fluorouracil (or 5-fluorouracil or 5-FU), methotrexate, edatrexate (10-ethyl-10-deazaaminopterin), thiotepa, carboplatin, cisplatin, taxanes, paclitaxel, protein-bound paclitaxel, docetaxel, vinorelbine, tamoxifen, raloxifene, toremifene, fulvestrant, gemcitabine, irinotecan, ixabepilone, temozolmide, topotecan, vincristine, vinblastine, eribulin, mutamycin, capecitabine, anastrozole, exemestane, letrozole, leuprolide, abarelix, buserlin, goserelin, megestrol acetate, risedronate, pamidronate, ibandronate, alendronate, denosumab, zoledronate, trastuzumab, tykerb, anthracyclines, bevacizumab, aldesleukin, cobimetinib, dabrafenib, dacarbazine, talimogene laherparepvec, imiquimod, recombinant Interferon Alfa-2b, ipilimumab, pembrolizumab, trametinib, nivolumab, peginterferon Alfa-2b, sonidegib, vismodegib, vemurafenib, cetuximab, irinotecan hydrochloride, leucovorin calcium, trifluridine and tipiracil hydrochloride, oxaliplatin, panitumumab, ramucirumab, regorafenib, and ziv-aflibercept.

Kits

The present disclosure provides kits for detecting one or more mutations in the plurality of hereditary cancer-related genes described herein, in a dried biological fluid sample. In some embodiments, the kits comprise a skin puncture tool, a volumetric absorptive microsampling device, a lysis buffer, and proteinase K, wherein the plurality of hereditary cancer-related genes comprises APC, ATM, BARD1, BMPR1A, BRCA1, BRCA2, BRIP1, CDH1, CDK4, CDKN2A (p14ARF and p16), CHEK2, EPCAM MEN1, MLH1, MSH2, MSH6, MUTYH, NBN, NF1, PALB2, PMS2, POLD1, POLE, PTEN, RAD51C, RAD51D, RET, SDHB, SDHC, SDHD, SMAD4, STK11, TP53, and VHL. The lysis buffer may comprise guanidine hydrochloride, Tris.Cl, EDTA, Tween 20, and Triton X-100. Alternatively, the lysis buffer may comprise 2.5-10% sodium dodecyl sulphate.

In some embodiments, the kits further comprise one or more components for denaturing nucleoprotein complexes in cells present in the dried biological fluid sample. Additionally or alternatively, in some embodiments, the kits further comprise one or more components for removing protein contaminants, inactivating nuclease activity, and/or removing biological and/or chemical contaminants present in the dried biological fluid sample.

In some embodiments, the kits further comprise one or more primer pairs that hybridize to one or more regions or exons of one or more of the plurality of hereditary cancer-related genes. Additionally or alternatively, in some embodiments, the kits further comprise one or more bait sequences that hybridize to one or more regions or exons of one or more of the plurality of hereditary cancer-related genes.

Particularly, in some embodiments, kits of the present technology comprise one or more primer pairs or bait sequences that selectively hybridize to, and are useful in amplifying or capturing one or more of the genes selected from the group consisting of APC, ATM, BARD1, BMPR1A, BRCA1, BRCA2, BRIP1, CDH1, CDK4, CDKN2A (p14ARF and p16), CHEK2, EPCAM MEN1, MLH1, MSH2, MSH6, MUTYH, NBN, NF1, PALB2, PMS2, POLD1, POLE, PTEN, RAD51C, RAD51D, RET, SDHB, SDHC, SDHD, SMAD4, STK11, TP53, and VHL.

In some embodiments, the kits of the present technology comprise a single primer pair or bait sequence that hybridizes to a region or exon of a single gene selected from the group consisting of APC, ATM, BARD1, BMPR1A, BRCA1, BRCA2, BRIP1, CDH1, CDK4, CDKN2A (p14ARF and p16), CHEK2, EPCAM, MEN1, MLH1, MSH2, MSH6, MUTYH, NBN, NF1, PALB2, PMS2, POLD1, POLE, PTEN, RAD51C, RAD51D, RET, SDHB, SDHC, SDHD, SMAD4, STK11, TP53, and VHL. In other embodiments, the kits of the present technology comprise multiple primer pairs or bait sequences that hybridize to one or more regions or exons of a single gene selected from the group consisting of APC, ATM, BARD1, BMPR1A, BRCA1, BRCA2, BRIP1, CDH1, CDK4, CDKN2A (p14ARF and p16), CHEK2, EPCAM, MEN1, MLH1, MSH2, MSH6, MUTYH, NBN, NF1, PALB2, PMS2, POLD1, POLE, PTEN, RAD51C, RAD51D, RET, SDHB, SDHC, SDHD, SMAD4, STK11, TP53, and VHL. In certain embodiments, the kits of the present technology comprise multiple primer pairs or bait sequences comprising a single primer pair or bait sequence that specifically hybridizes to a region or exon of a single gene for each of APC, ATM, BARD1, BMPR1A, BRCA1, BRCA2, BRIP1, CDH1, CDK4, CDKN2A (p14ARF and p16), CHEK2, EPCAM, MEN1, MLH1, MSH2, MSH6, MUTYH, NBN, NF1, PALB2, PMS2, POLD1, POLE, PTEN, RAD51C, RAD51D, RET, SDHB, SDHC, SDHD, SMAD4, STK11, TP53, and VHL. In certain embodiments, the kits of the present technology comprise multiple primer pairs or bait sequences comprising more than one primer pair or more than one bait sequence that hybridizes to one or more regions or exons for each of APC, ATM, BARD1, BMPR1A, BRCA1, BRCA2, BRIP1, CDH1, CDK4, CDKN2A (p14ARF and p16), CHEK2, EPCAM, MEN1, MLH1, MSH2, MSH6, MUTYH, NBN, NF1, PALB2, PMS2, POLD1, POLE, PTEN, RAD51C, RAD51D, RET, SDHB, SDHC, SDHD, SMAD4, STK11, TP53, and VHL.

Thus, it is contemplated herein that the kits of the present technology can comprise primer pairs or bait sequences that recognize and specifically hybridize to one or more regions or exons of one or more genes selected from the group consisting APC, ATM, BARD1, BMPR1A, BRCA1, BRCA2, BRIP1, CDH1, CDK4, CDKN2A (p14ARF and p16), CHEK2, EPCAM, MEN1, MLH1, MSH2, MSH6, MUTYH, NBN, NF1, PALB2, PMS2, POLD1, POLE, PTEN, RAD51C, RAD51D, RET, SDHB, SDHC, SDHD, SMAD4, STK11, TP53, and VHL.

In any of the above embodiments of the kits of the present technology, the volumetric absorptive microsampling device is a MITRA® tip.

In some embodiments, the kits may comprise a plurality of volumetric absorptive microsampling devices, each having a hollow holder at the proximal end and an absorbent tip at the distal end. The absorbent tip comprises a hydrophilic, polymeric material configured to absorb 30 microliters or less of blood within about 10 seconds or less. The kit also includes a container having a plurality of compartments. Each compartment is configured to releasably engage a volumetric absorptive microsampling device. The container is configured to prevent the absorbent tips of the microsampling devices from abutting the compartment within which the microsampling device is placed.

Additionally or alternatively, in certain embodiments, the kits may include a plurality of access ports with each port associated with an individual compartment. Each port is located to allow printing onto the holder of a volumetric absorptive microsampling device present within the compartment with which the port is associated. In certain embodiments, the holder of a volumetric absorptive microsampling device has a plurality of ribs extending along a length of the holder with the ribs configured to keep the absorbent tip from contacting walls of the container. The container preferably has two parts configured to form tubular shaped compartments. The container may have a first part with a plurality of elongated mounting protrusions each extending along a portion of a different compartment. The hollow end of the holder of the volumetric absorptive microsampling device fits onto the mounting protrusion to releasably fasten the holder onto the mounting protrusion.

In some embodiments, the kit comprises liquid medium containing the at least one target-specific nucleic acid probe in a concentration of 250 nM or less. With such a kit, the probes are provided in the required amount to perform reliable multiplex detection reactions according to the present technology.

In some embodiments, the kits further comprise buffers, enzymes having polymerase activity, enzymes having polymerase activity and lacking 5'→3' exonuclease activity or both 5'→3' and 3'→5' exonuclease activity, enzyme cofactors such as magnesium or manganese, salts, chain extension nucleotides such as deoxynucleoside triphosphates (dNTPs), modified dNTPs, nuclease-resistant dNTPs or labeled dNTPs, necessary to carry out an assay or reaction, such as amplification and/or detection of one or more mutations in the plurality of hereditary cancer-related genes described herein, in a dried biological fluid sample.

In one embodiment, the kits of the present technology further comprise a positive control nucleic acid sequence and a negative control nucleic acid sequence to ensure the integrity of the assay during experimental runs. The kit may also comprise instructions for use, software for automated analysis, containers, packages such as packaging intended for commercial sale and the like.

The kit may further comprise one or more of: wash buffers and/or reagents, hybridization buffers and/or reagents, labeling buffers and/or reagents, and detection means. The buffers and/or reagents are usually optimized for the particular amplification/detection technique for which the kit is intended. Protocols for using these buffers and reagents for performing different steps of the procedure may also be included in the kit.

The kits of the present technology may include components that are used to prepare nucleic acids from a dried biological fluid sample for the subsequent amplification and/or detection of alterations in target nucleic acid sequences corresponding to the plurality of hereditary cancer-related genes disclosed herein. Such sample preparation components can be used to produce nucleic acid extracts from dried biological fluid samples, such as dried serum, dried plasma, or dried whole blood. The test samples used in the above-described methods will vary based on factors such as the assay format, nature of the detection method, and the specific cells or extracts used as the test sample to be assayed. Methods of extracting nucleic acids from samples are well known in the art and can be readily adapted to obtain a sample that is compatible with the system utilized. Automated sample preparation systems for extracting nucleic acids from a test sample are commercially available, e.g., Roche Molecular Systems' COBAS AmpliPrep System, Qiagen's BioRobot 9600, Qiagen's BioRobot EZ1, QIAsymphony®, and Applied Biosystems' PRISM™ 6700 sample preparation system.

EXAMPLES

Example 1: Extraction of Genomic DNA from Dried Blood Samples Collected Using MITRA® Tips This Example demonstrates that the methods of the present technology are useful for extracting high yields of genomic DNA from a dried biological fluid sample (e.g., dried blood) collected using a volumetric absorptive microsampling device.

A total of four human subjects were enrolled in the study. Three MITRA® tips of blood were collected from each of 4 blood donors in order to simultaneously test three extraction methods. A fixed volume of 10 μL of blood was collected on each MITRA® Tip collection device via fingerstick. After drying the blood samples, the absorbent tips of the MITRA® Tip collection devices were then placed in 180 μL Buffer G2 (a lysis buffer containing 800 mM guanidine hydrochloride; 30 mM Tris.Cl, pH 8.0; 30 mM EDTA, pH 8.0; 5% Tween 20; 0.5% Triton X-100) and were vortexed for 15 seconds. The remaining sample processing steps for each of the three extraction methods are summarized below:

| Step | Method 1 | Method 2 | Method 3 |
|---|---|---|---|
| 1 | Incubate MITRA ® Tip in Buffer G2 at 90° C. for 15 min | — | Incubate MITRA ® Tip in Buffer G2 at 90° C. for 15 min |
| 2 | Vortex for 15 sec | — | Vortex for 15 sec |
| 3 | Add 10 μL Proteinase K | | |
| 4 | Vortex for 15 sec | | |
| 5 | Incubate with Proteinase K at 56° C. for 1 hour | Incubate with Proteinase K at 56° C. for 1 hour | Incubate with Proteinase K at 56° C. Overnight |
| 6 | Vortex 15 sec | | |
| 7 | Aliquot cell lysate to new tube | | |
| 8 | Perform remaining genomic DNA extraction on EZ1 ® Biorobot using Tissue DNA protocol | | |

Extracted genomic DNA was then quantified using Qubit® dsDNA HS Assay Kit, which uses a dsDNA intercalating dye that only fluoresces in the presence of dsDNA. Therefore, quantitation of dsDNA using the Qubit® dsDNA HS Assay Kit is not affected by RNA, proteins, salts, or other contaminants that may affect other quantitation methods. Table 1 and FIG. 1 demonstrate that the DNA yield obtained from each MITRA® tip varied according to the extraction method. It was determined that extraction method 3 (Incubation of MITRA® Tip with Buffer G2 at 90° C. for 15 min, and with Proteinase K at 56° C. overnight) yielded the highest quantity of DNA.

TABLE 1

Range of DNA yield obtained per MITRA ® Tip

| Extraction Method | Total DNA yield (ng) |
|---|---|
| 1 | 111-248 |
| 2 | 163-210 |
| 3 | 222-390 |

Figure 3:
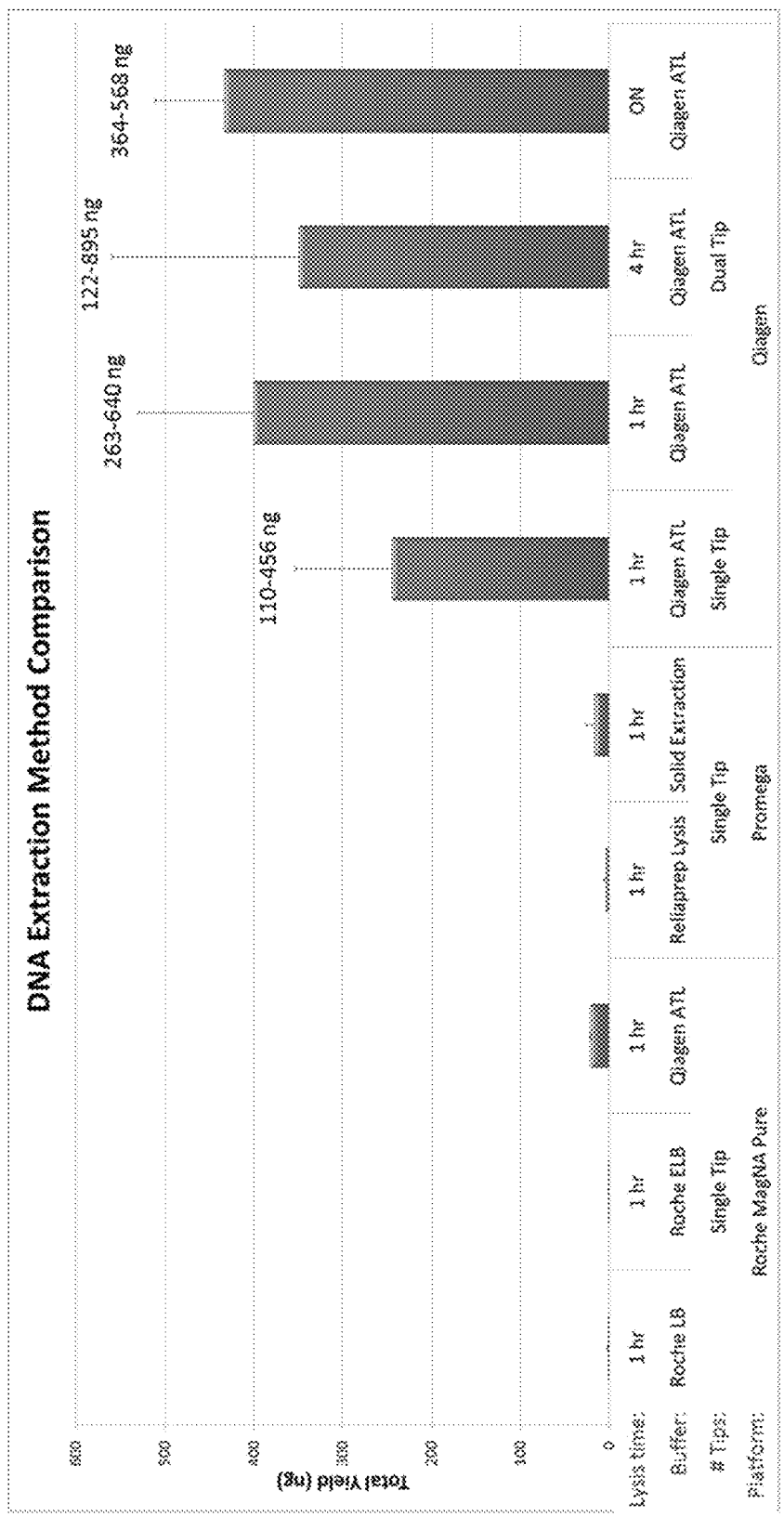
FIG. 3 shows a comparison of DNA yields obtained from MITRA® tips when using different DNA extraction methods. 'ON' means the samples were incubated with a particular lysis buffer overnight.

Additionally, FIG. 3 demonstrates that DNA yields recovered from MITRA® Tips would vary significantly depending on the lysis buffer, lysis period, extraction platform, and the number of MITRA® Tips utilized during extraction procedure. For example, DNA yields recovered from a single MITRA® Tip incubated with Qiagen ATL buffer (comprising 2.5-10% sodium dodecyl sulphate) for 1 hour was higher in the Qiagen platform (between 110-456 ng) compared to the Roche MagNA Pure platform (<30 ng). In contrast, DNA yields obtained with certain lysis buffers, such as Roche Lysis Buffer, Roche External Lysis Buffer, and Reliaprep™ (Promega), were low (<10 ng). See FIG. 3.

These results demonstrate that the methods of the present technology are useful for extracting high yields of genomic DNA from a dried biological fluid sample (e.g., dried blood) collected using a volumetric absorptive microsampling device.

Example 2: Detection of Hereditary Cancer-Related Mutations Using Dried Blood Samples Extracted from MITRA® Tips Genomic DNA was extracted from dried blood samples collected from each donor via MITRA® tips using extraction method 3 (incubation of MITRA® Tip with Buffer G2 at 90° C. for 15 min, and with Proteinase K at 56° C. overnight) as described in Example 1. DNA extracted from 2 MITRA® tips per donor was pooled. Pooled DNA was then tested on the MyVantage™ Hereditary Comprehensive Cancer Panel, which assesses 731 amplicons corresponding to a plurality of 34 hereditary cancer-related genes comprising APC, ATM, BARD1, BMPR1A, BRCA1, BRCA2, BRIP1, CDH1, CDK4, CDKN2A (p14ARF and p16), CHEK2, EPCAM MEN1, MLH1, MSH2, MSH6, MUTYH, NBN, NF1, PALB2, PMS2, POLD1, POLE, PTEN, RAD51C, RAD51D, RET, SDHB, SDHC, SDHD, SMAD4, STK11, TP53, and VHL. Next generation sequencing was performed on the Illumina NextSeq® Sequencer. Quality metrics for assessing successful sequencing of a covered region included a minimum of 20 reads per covered position in a given region.

Results.

Figure 2B:
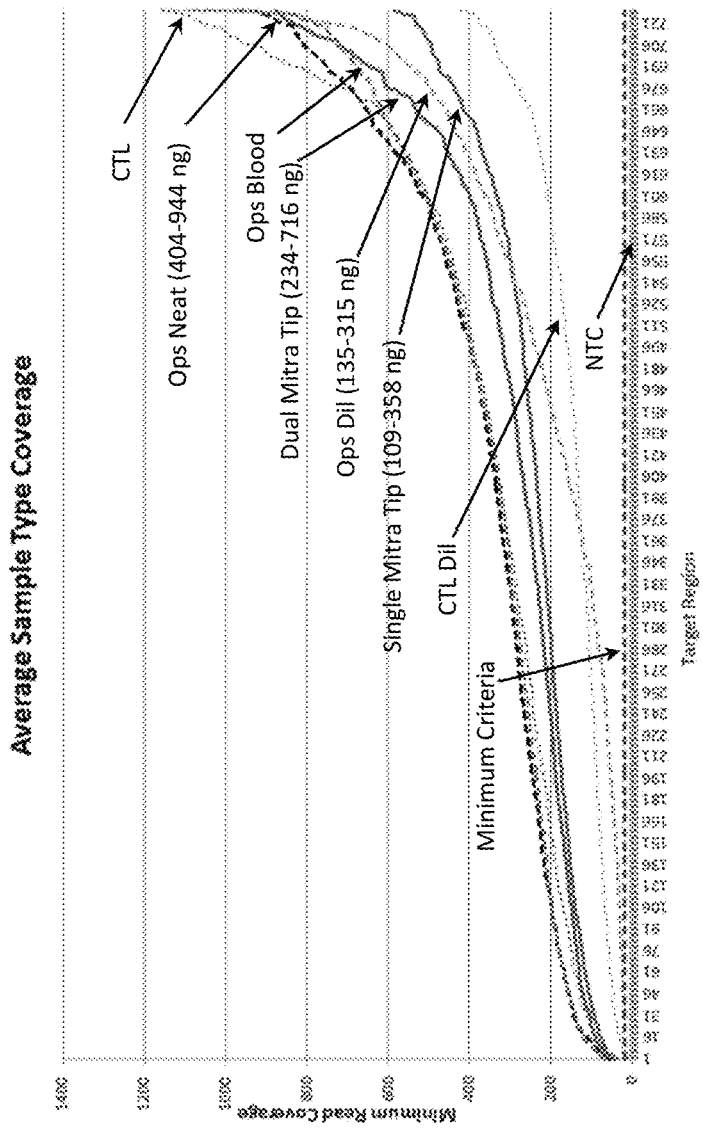
FIG. 2(b) shows the minimum read coverage per target region with dried blood samples obtained using single or dual-MITRA® tip extraction on a 34-gene cancer predisposition panel (MyVantage™ Hereditary Comprehensive Cancer Panel). "Ops" refers to routine operational samples.
Figure 4A:
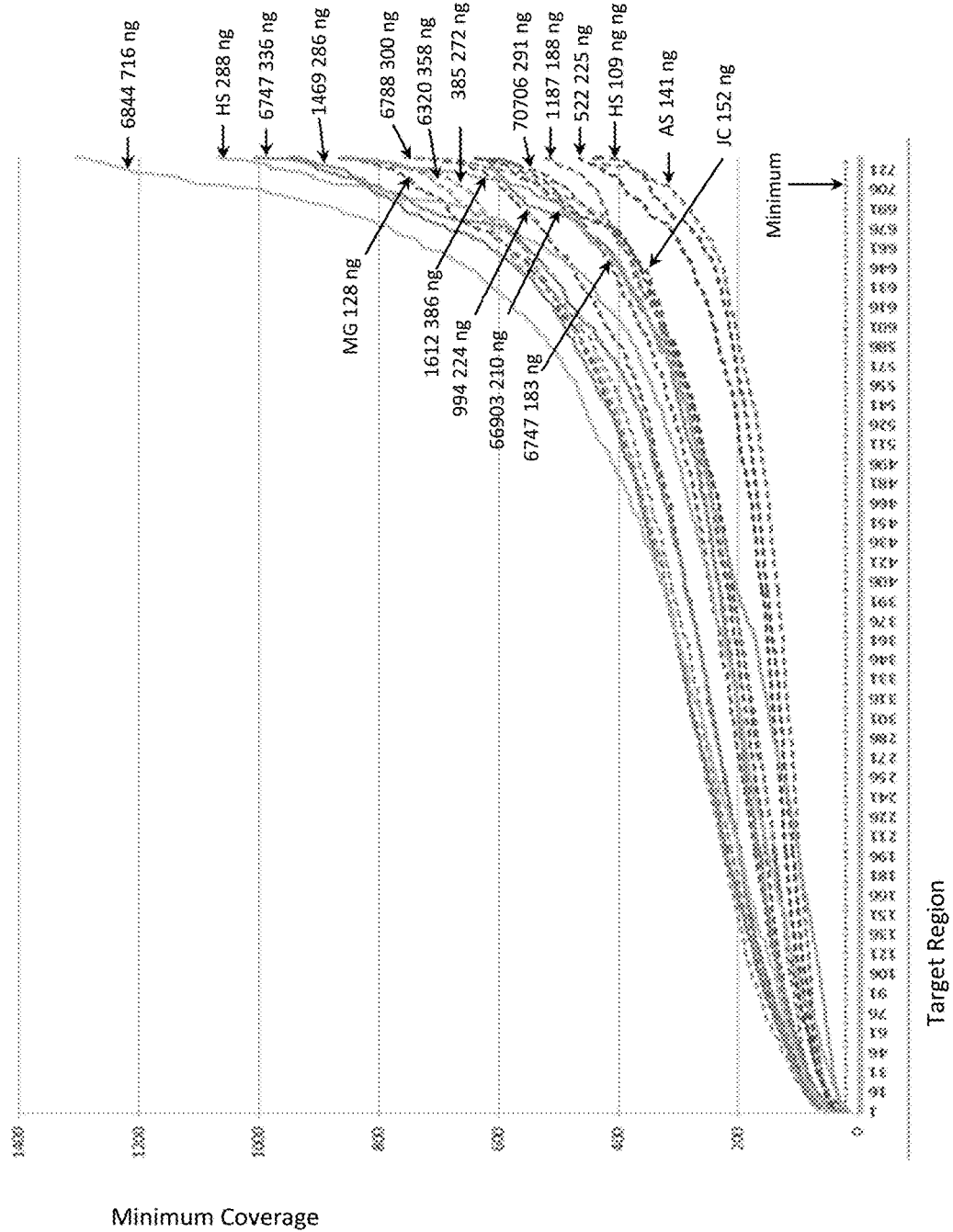
FIG. 4(a) shows the minimum read coverage per target region obtained from dried blood samples eluted from a single MITRA® tip (DNA yields ranging between 109-358 ng) on a 34-gene cancer predisposition panel (MyVantage™ Hereditary Comprehensive Cancer Panel). DNA extraction was performed using the QIAsymphony® platform.
Figure 4B:
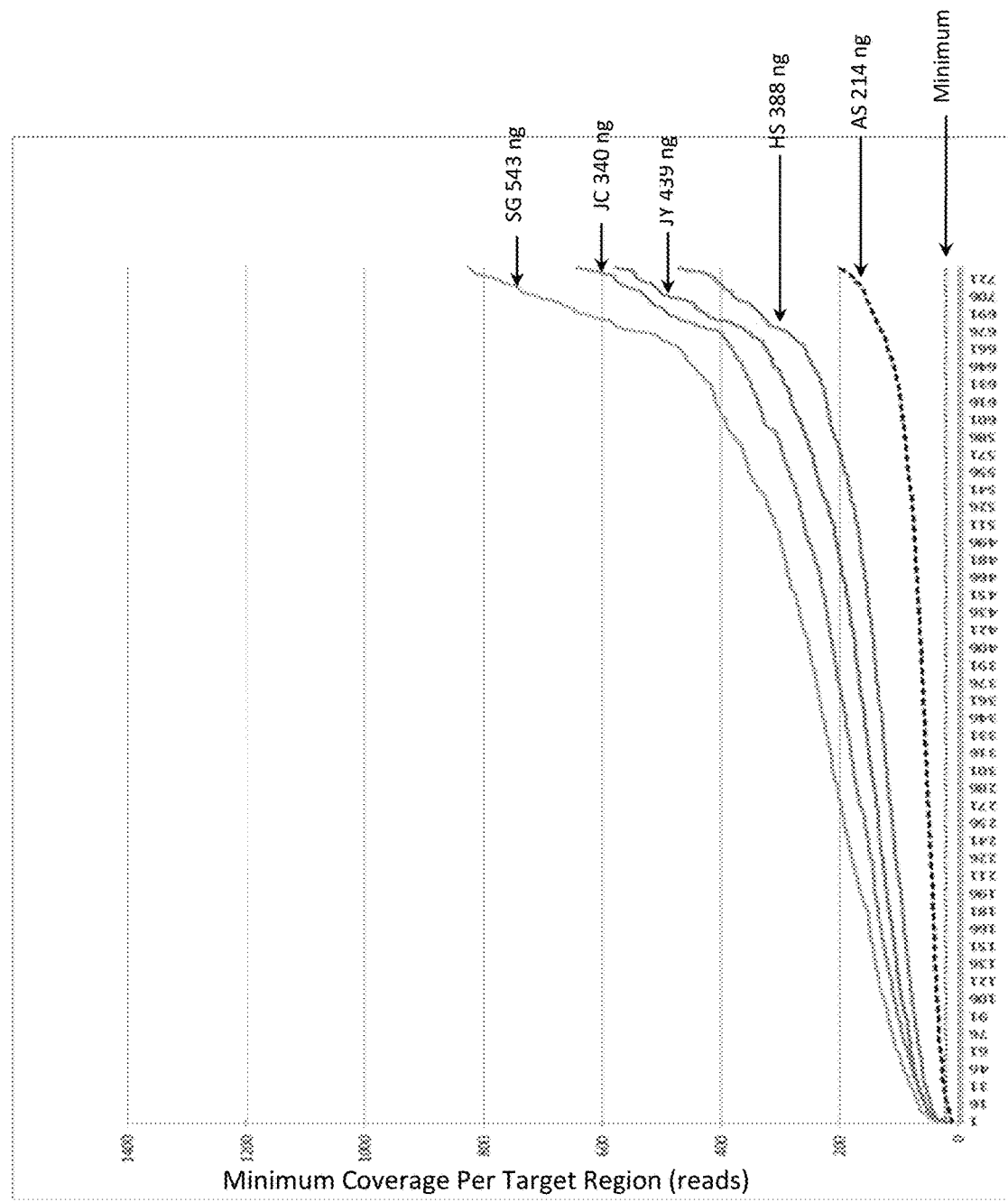
FIG. 4(b) shows the minimum read coverage per target region with dried blood samples obtained using single or dual-MITRA® tip extraction on a 34-gene cancer predisposition panel (MyVantage™ Hereditary Comprehensive Cancer Panel). 4 samples were subjected to dual-MITRA® tip extraction and resulted in DNA yields ranging between 340-543 ng. 1 sample (AS) was subjected to single tip extraction and had a DNA yield of 214 ng.

FIG. 2(a) shows that 100% of the 731 assessed regions had passed the QC criteria in three samples. One sample had 730 out of 731 assessed regions pass the QC criteria. The sequencing performance of samples subjected to single tip versus dual tip extraction was also compared. FIG. 2(b) and FIG. 4(b) show that 100% of the 731 assessed regions had passed the QC criteria, regardless of whether single tip extraction or dual tip extraction was employed.

Figure 5:
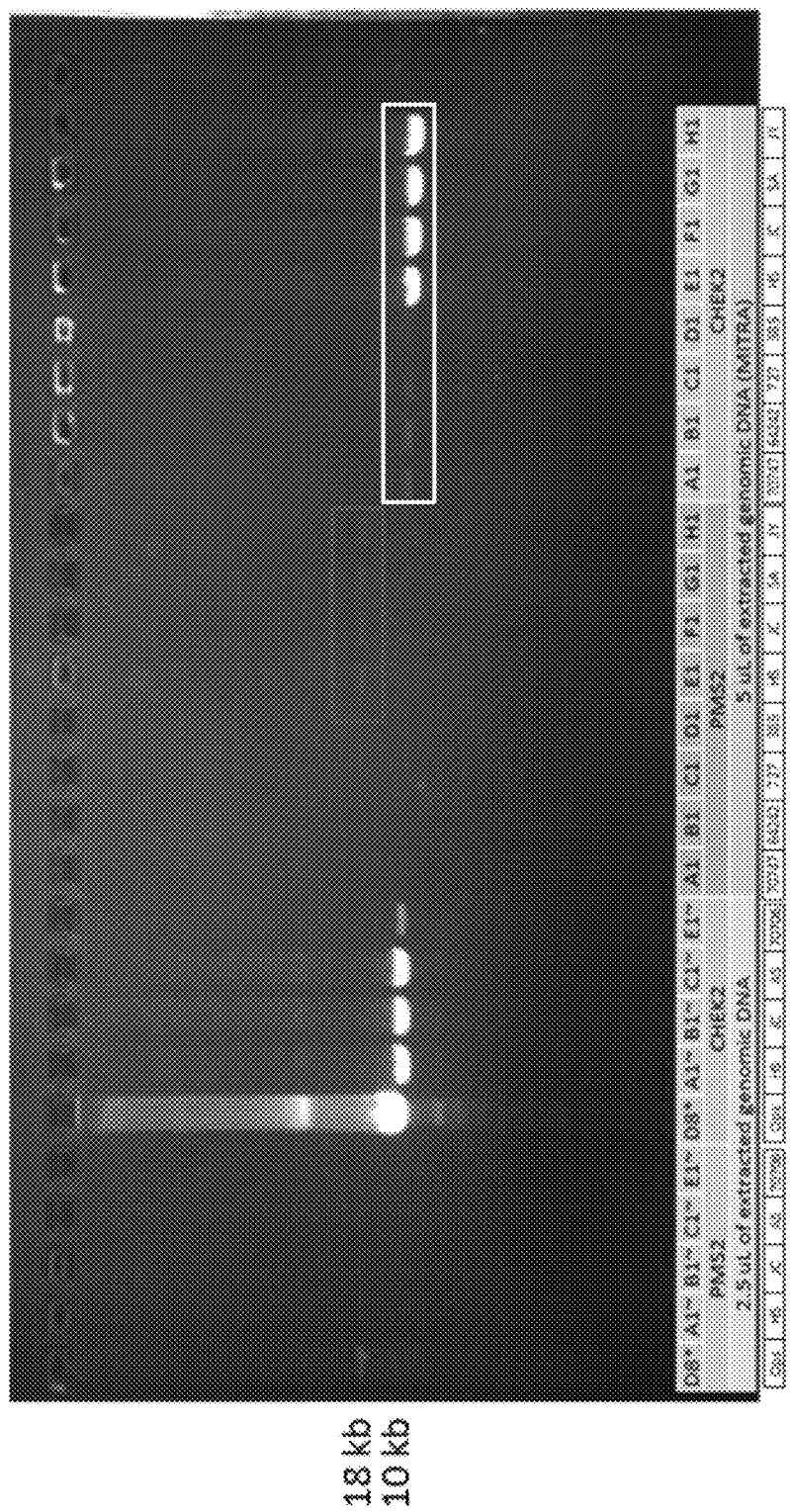
FIG. 5 shows the effective amplification of 10 kb and 18 kb regions corresponding to CHEK2 and PMS2 target regions respectively, via long-range PCR when using dried blood samples eluted from MITRA® tips.
Figure 6:
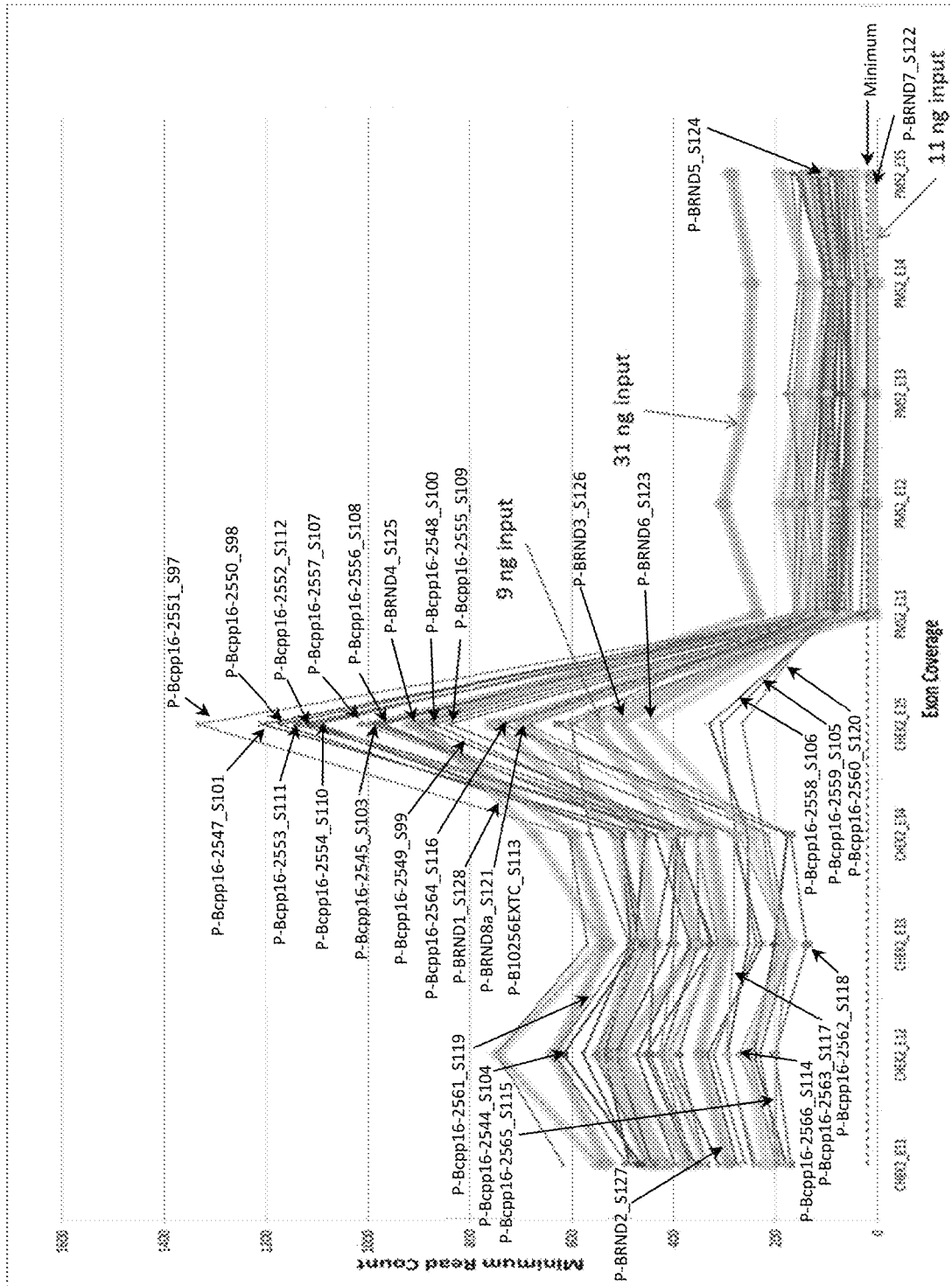
FIG. 6 shows the minimum read coverage of various CHEK2 and PMS2 exons obtained from dried blood samples eluted from MITRA® tips.

FIG. 5 demonstrates that 10 kb and 18 kb amplicons corresponding to CHEK2 and PMS2 target regions respectively, were effectively amplified via long-range PCR when using dried blood samples eluted from MITRA® tips. FIG. 6 demonstrates that genomic DNA extracted from dried blood samples eluted from MITRA® tips showed sufficient coverage of several CHEK2 and PMS2 exons.

Figure 7:
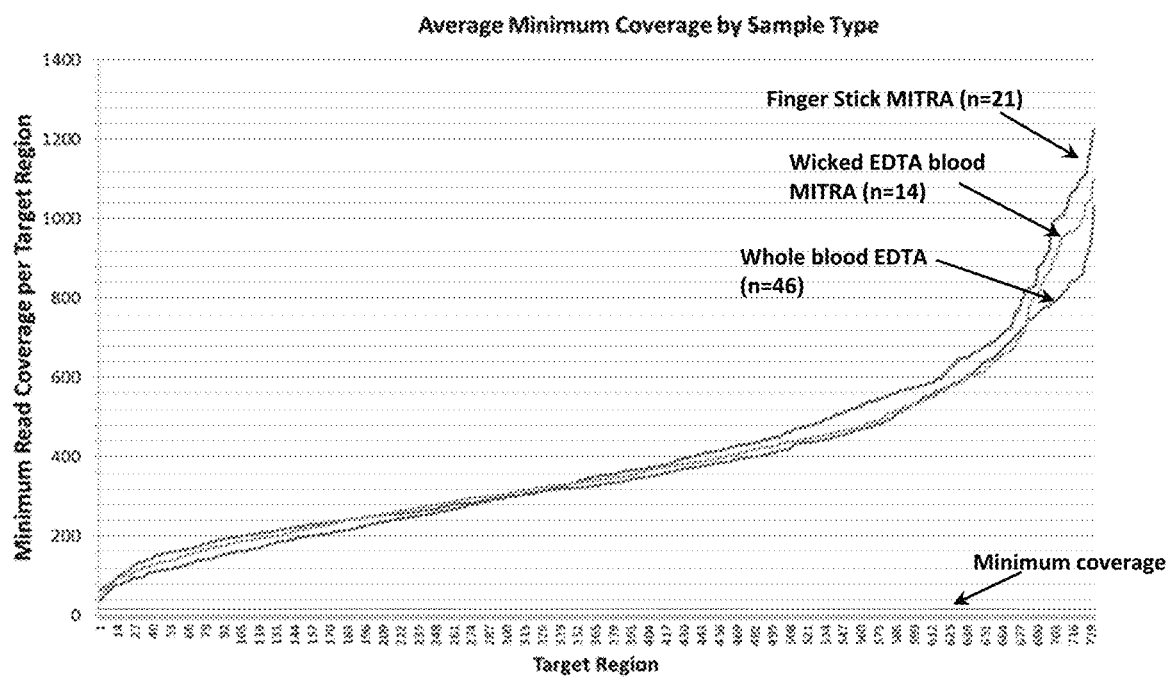
FIG. 7 shows the minimum read coverage per target region using DNA obtained from (a) blood collected by MITRA® tips via fingerstick, (b) MITRA® tips wicked with EDTA whole blood, and (c) EDTA whole blood obtained from conventional blood draws.

Further, FIG. 7 demonstrates that the minimum read coverage per target region using DNA obtained from MITRA® tips wicked with EDTA whole blood was comparable to that observed with DNA obtained from blood collected by MITRA® tips via fingerstick. Thus, these results demonstrate that the methods of the present technology are effective in detecting hereditary cancer-related mutations in dried biological fluid samples containing known PCR-inhibitors such as EDTA.

These results demonstrate that the methods of the present technology are capable of detecting at least one mutation in the plurality of hereditary cancer-related genes described herein, in a small-volume dried biological fluid sample that is collected with a volumetric absorptive microsampling device (e.g., MITRA® Tip).

Example 3: Detection of Hereditary Cancer-Related Mutations Using Dried Blood Samples Extracted from MITRA® Tips Via QIAsymphony® Platform Genomic DNA was extracted from 20 µL dried blood samples collected via MITRA® tips using the QIAsymphony® platform (which permits automation of 96 samples at a time). MITRA® tips were incubated with Qiagen ATL buffer overnight at 56° C. DNA extraction was subsequently performed on the QIAsymphony® platform according to manufacturer's instructions. All samples were subjected to single tip extraction, and resulted in DNA yields ranging between 109-358 ng. DNA was then tested on the MyVantage™ Hereditary Comprehensive Cancer Panel and next generation sequencing was performed on the Illumina NextSeq® Sequencer. Quality metrics for assessing successful sequencing of a covered region included a minimum of 20 reads per covered position in a given region.

Results. FIG. 4(a) demonstrates that DNA input levels as low as 109 ng (obtained from a single MITRA® tip) displayed sufficient coverage on the MyVantage™ Hereditary Comprehensive Cancer Panel for both single nucleotide variation (SNV) and insertion/deletion (INDEL) detection.

These results demonstrate that the methods of the present technology are capable of detecting at least one mutation in the plurality of hereditary cancer-related genes described herein, in a small-volume dried biological fluid sample that is collected with a volumetric absorptive microsampling device (e.g., MITRA® Tip).

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

The terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure claimed.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

The invention claimed is:

1. A method for detecting the presence or absence of mutations in a plurality of hereditary cancer-related genes in a pooled sample comprising:
   (a) eluting at least two dried biological fluid samples, each containing no more than 400 ng of genomic DNA, from at least two absorbent tips of microsampling devices, each of the at least absorbent tips comprising a separate dried biological fluid sample, by contacting the least two absorbent tips of the microsampling devices with a Proteinase K and a lysis buffer comprising guanidine hydrochloride, Tris.Cl, EDTA, Tween 20, and Triton X-100;
   (b) extracting genomic DNA from the at least two dried biological fluid samples; to obtain at least two nucleic acid samples;
   (c) generating at least two libraries of amplicons from each of the at least two nucleic acid samples, wherein each of the at least two libraries of amplicons comprises sequences corresponding to at least six and up to all of APC, ATM, BARD1, BMPR1A, BRCA1, BRCA2, BRIP1, CDH1, CDK4, CDKN2A (p14ARF and p16), CHEK2, EPCAM, MEN1, MLH1, MSH2, MSH6, MUTYH, NBN, NF1, PALB2, PMS2, POLD1, POLE, PTEN, RAD51C, RAD51D, RET, SDHB, SDHC, SDHD, SMAD4, STK11, TP53, and VHL, wherein an index sequence is ligated to at least one end of the amplicons;
   (d) pooling the at least two libraries of amplicons to form a pooled library of amplicons; and
   (e) detecting the presence or absence of mutations in the pooled library of amplicons using high throughput massive parallel sequencing.

2. The method of claim 1, wherein the dried biological fluid sample is obtained from a patient having or suspected of having a hereditary cancer.

3. The method of claim 1, wherein the dried biological fluid sample is dried plasma, dried serum, or dried whole blood.

4. The method of claim 1, wherein the dried biological fluid sample is collected from a patient via fingerstick.

5. The method of claim 1, wherein elution of the dried biological fluid sample is performed by contacting the absorbent tip of the microsampling device with the lysis buffer for up to 15 minutes at 90° C.

6. The method of claim 1, wherein elution of the dried biological fluid sample is performed by contacting the absorbent tip of the microsampling device with Proteinase K for up to 1 hour at 56° C.

7. The method of claim 1, wherein elution of the dried biological fluid sample is performed by contacting the absorbent tip of the microsampling device with Proteinase K for up to 18 hours at 56° C.

8. The method of claim 1, wherein the sample volume of the microsampling device is no more than 20 µL.

9. The method of claim 2, wherein the hereditary cancer is breast cancer, ovarian cancer, colon cancer, or skin cancer.

10. The method of claim 1, wherein about 100 ng to about 400 ng of genomic DNA is eluted from the absorbent tip of the microsampling device.

11. The method of claim 1, wherein the high throughput massive parallel sequencing is performed using pyrosequencing, reversible dye-terminator sequencing, SOLiD sequencing, Ion semiconductor sequencing, Helioscope single molecule sequencing, sequencing by synthesis, sequencing by ligation, or SMRT™ sequencing.

12. The method of claim 1, wherein the adapter sequence is a P5 adapter, P7 adapter, P1 adapter, A adapter, or Ion Xpress™ barcode adapter.

13. The method of claim 1, wherein the plurality of amplicons are enriched using a bait set comprising nucleic acid sequences that are complementary to at least one of the amplicons in the plurality of amplicons.

14. The method of claim 13, wherein the nucleic acid sequences of the bait set are RNA baits, DNA baits, or a combination thereof.

15. A method for detecting the presence or absence of mutations in a plurality of hereditary cancer-related genes in a pooled nucleic acid sample comprising generating a library from a pooled nucleic acid sample comprising amplicons corresponding to at least six and up to all of APC, ATM, BARD1, BMPR1A, BRCA1, BRCA2, BRIP1, CDH1, CDK4, CDKN2A (p14ARF and p16), CHEK2, EPCAM, MEN1, MLH1, MSH2, MSH6, MUTYH, NBN, NF1, PALB2, PMS2, POLD1, POLE, PTEN, RAD51C, RAD51D, RET, SDHB, SDHC, SDHD, SMAD4, STK11, TP53, and VHL, and detecting the presence of absence of at least one mutation in the plurality of hereditary cancer-related genes using high throughput massive parallel sequencing; wherein the pooled nucleic acid sample was extracted from dried biological fluid samples obtained from at least two subjects and eluted from an absorbent tip of a microsampling device by contacting the absorbent tip of the microsampling device with (i) a lysis buffer comprising guanidine hydrochloride, Tris.Cl, EDTA, Tween 20, and Triton X-100 and (ii) Proteinase K, wherein no more than 400 ng of genomic DNA is eluted from the absorbent tip of the microsampling device.

16. A method for selecting a patient exhibiting cancer symptoms, or a patient at risk for hereditary cancer, for treatment with an anti-cancer therapeutic agent comprising
    (a) eluting a dried blood sample from a absorbent tip of a volumetric microsampling device by contacting the absorbent tip with a Proteinase K and a lysis buffer comprising guanidine hydrochloride, Tris.Cl, EDTA, Tween 20, and Triton X-100 under conditions that result in the release of genomic DNA from blood cells, wherein the dried blood sample was collected from the patient with the volumetric absorptive microsampling device, wherein no more than 400 ng of genomic DNA is eluted from the absorbent tip of the microsampling device;
    (b) isolating genomic DNA from the eluted dried blood sample;
    (c) generating a library of amplicons corresponding to at least six and up to all of APC, ATM, BARD1, BMPR1A, BRCA1, BRCA2, BRIP1, CDH1, CDK4, CDKN2A (p14ARF and p16), CHEK2, EPCAM, MEN1, MLH1, MSH2, MSH6, MUTYH, NBN, NF1, PALB2, PMS2, POLD1, POLE, PTEN, RAD51C, RAD51D, RET, SDHB, SDHC, SDHD, SMAD4, STK11, TP53, and VHL, wherein an index sequence is ligated to at least one end of the amplicons;
    (d) pooling the library of amplicons generated from the patient with at least one other library of amplicons to form a pooled library of amplicons;
    (e) detecting the presence or absence of mutations in the pooled library of amplicons using high throughput massive parallel sequencing; and
    (f) selecting the patient for treatment with an anti-cancer therapeutic agent, if a mutation in at least one of the library of amplicons is detected.

17. The method of claim 16, wherein the patient has or is at risk of developing a hereditary cancer selected from the group consisting of breast cancer, ovarian cancer, skin cancer, or colon cancer.

18. The method of claim 16, wherein the anti-cancer therapeutic agent is one or more agents selected from the group consisting of cyclophosphamide, fluorouracil (or 5-fluorouracil or 5-FU), methotrexate, edatrexate (10-ethyl-10-deaza-aminopterin), thiotepa, carboplatin, cisplatin, taxanes, paclitaxel, protein-bound paclitaxel, docetaxel, vinorelbine, tamoxifen, raloxifene, toremifene, fulvestrant, gemcitabine, irinotecan, ixabepilone, temozolmide, topotecan, vincristine, vinblastine, eribulin, mutamycin, capecitabine, anastrozole, exemestane, letrozole, leuprolide, abarelix, buserlin, goserelin, megestrol acetate, risedronate, pamidronate, ibandronate, alendronate, denosumab, zoledronate, trastuzumab, tykerb, anthracyclines, bevacizumab, aldesleukin, cobimetinib, dabrafenib, dacarbazine, talimogene laherparepvec, imiquimod, recombinant Interferon Alfa-2b, ipilimumab, pembrolizumab, trametinib, nivolumab, peginterferon Alfa-2b, sonidegib, vismodegib, vemurafenib, cetuximab, irinotecan hydrochloride, leucovorin calcium, trifluridine and tipiracil hydrochloride, oxaliplatin, panitumumab, ramucirumab, regorafenib, and ziv-aflibercept.

* * * * *

UNITED STATES PATENT AND TRADEMARK OFFICE
CERTIFICATE OF CORRECTION

PATENT NO. : 11,441,188 B2
APPLICATION NO. : 15/811515
DATED : September 13, 2022
INVENTOR(S) : Heather Sanders and Nigel J. Clarke It is certified that error appears in the above-identified patent and that said Letters Patent is hereby corrected as shown below:

In the Claims

Column 29, Claim 1, Lines 54-55, "Tween 20, and Triton X-100" should be --and a nonionic surfactant--.

Column 30, Claim 11, Lines 38-39, delete "SOLiD sequencing, Ion semiconductor sequencing, Helioscope" should be --Ion semiconductor sequencing--.

Column 30, Claim 11, Line 41, "SMRT™" should be --next generation--.

Column 30, Claim 12, Lines 43-44, "Ion Xpress™" should be --a--.

Column 31, Claim 15, Lines 3-4, "Tween 20, and Triton X-100" should be --and a nonionic surfactant--.

Column 31, Claim 16, Line 14, "Tween 20, and Triton X-100" should be --and a nonionic surfactant--.

Signed and Sealed this
Twenty-first Day of March, 2023

Katherine Kelly Vidal
*Director of the United States Patent and Trademark Office*